(12) United States Patent
Ishige et al.

(10) Patent No.: US 6,403,293 B2
(45) Date of Patent: Jun. 11, 2002

(54) SILVER HALIDE COLOR PHOTOGRAPHIC LIGHT SENSITIVE MATERIAL

(75) Inventors: Osamu Ishige; Emiko Kataoka; Hiroyuki Hoshino, all of Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/733,376

(22) Filed: Dec. 8, 2000

(30) Foreign Application Priority Data

Dec. 16, 1999 (JP) .......................................... 11-357501

(51) Int. Cl.$^7$ ................................................. G03C 1/46
(52) U.S. Cl. .................. 430/504; 430/555; 430/599; 430/600; 430/603; 430/607; 430/611; 430/544; 430/955; 430/957
(58) Field of Search ................................ 430/504, 555, 430/599, 600, 603, 607, 611, 544, 955, 957

(56) References Cited

U.S. PATENT DOCUMENTS

| | | | |
|---|---|---|---|
| 4,482,629 A | * 11/1984 | Nakagawa et al. | 430/544 |
| 4,782,012 A | * 11/1988 | DeSelms et al. | 430/544 |
| 4,853,319 A | * 8/1989 | Krishnamurthy et al. | 430/555 |
| 4,868,099 A | 9/1989 | Renner | |
| 5,126,234 A | * 6/1992 | Naruse et al. | 430/555 |
| 5,262,292 A | 11/1993 | Krishnamurthy | |
| 5,447,830 A | * 9/1995 | Pawlak et al. | 430/555 |
| 5,605,787 A | * 2/1997 | Pawlak et al. | 430/555 |
| 5,866,313 A | 2/1999 | Hirano | |

FOREIGN PATENT DOCUMENTS

| | | |
|---|---|---|
| EP | 0628868 | 12/1994 |
| EP | 0686872 | 12/1995 |
| EP | 0730197 | 4/1996 |

* cited by examiner

Primary Examiner—Geraldine Letscher
(74) Attorney, Agent, or Firm—Bierman, Muserlian and Lucas

(57) ABSTRACT

A silver halide color photographic light sensitive material is disclosed, comprising a support having thereon a blue-sensitive silver halide emulsion layer, a green-sensitive silver halide emulsion layer and a red-sensitive silver halide emulsion layers, wherein at least one of the silver halide emulsion layers contains a coupler represented by the following formula:

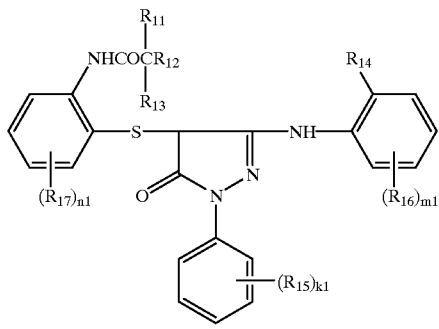

18 Claims, No Drawings

SILVER HALIDE COLOR PHOTOGRAPHIC LIGHT SENSITIVE MATERIAL

FIELD OF THE INVENTION

The present invention relates to sliver halide color photographic light sensitive materials and in particular to silver halide color photographic materials exhibiting enhanced sensitivity, superior color forming properties and improved storage stability.

BACKGROUND OF THE INVENTION

In conventional silver halide color photographic materials (hereinafter, also denoted as color photographic materials or simply as photographic materials), a subtractive color system is employed and color images are formed by the combination of three dyes derived from yellow, magenta and cyan couplers.

As magenta couplers used in conventional color photographic materials are known 5-pyrazolone, pylazolinobenzoimidazole or indanone type couplers, and of these, 5-pyrazolone derivatives are broadly employed.

Substituents at the 3-position of the 5-pyrazolone ring of the 5-pyrazolone derivatives include, for example, an alkyl group, an aryl group, an alkoxy group described in U.S. Pat. Nos. 2,369,489 and 2,600,788, an acylamino group, and a ureido group described in U.S. Pat. No. 3,558,319. However, such couplers had the disadvantages that coupling activity with an oxidation product of a developing agent was so low that sufficiently high magenta dye image density could be obtained, the magenta dye images obtained through color development resulted in a relatively high secondary absorption in the blue light region and the longer wavelength-side absorption near edge of the main absorption was not sharp.

Further, 3-anilino-5-pyrazolone couplers described in U.S. Pat. Nos. 2,311,081, 3,677,764 and 3,684,514; British patent Nos. 956,261 and 1,173,513, exhibited a relatively high coupling activity, giving a high color density and having advantages such as unwanted absorption in the red light region being relatively low. However, commonly known 3-anilino-5-pyrazolone type couplers have disadvantages that solubility in organic solvents is relatively low and when a color photographic material containing this coupler is aged, precipitation of the coupler tends to easily occur in the photographic material. Furthermore, color photographic materials containing commonly known 3-anilino-5-pyrazolone couplers exhibited a disadvantage that the magenta dye image density, after being processed, varied after being aged.

In commercially available color photographic materials, as is well known, a coupler is not used alone but is used in combination with various functional couplers to improve image quality and color reproducibility. As such functional couplers, so-called DIR couplers and masking couplers (or colored couplers) are generally employed. However, in cases when the 3-anilino-5-pyrazolone coupler is used in combination with a functional coupler, it was shown that the foregoing disadvantages tended to increase.

SUMMARY OF THE INVENTION

Accordingly, it is an object of the present invention to provide a silver halide color photographic light sensitive material exhibiting enhanced sensitivity, superior color forming property and improved storage stability.

The above object of the invention can be accomplished by the following constitution:

(1) A silver halide color photographic light sensitive material comprising a support having thereon blue-sensitive, green-sensitive and red-sensitive silver halide emulsion layers, wherein at least one of the silver halide emulsion layers contains a coupler represented by the following formula (I):

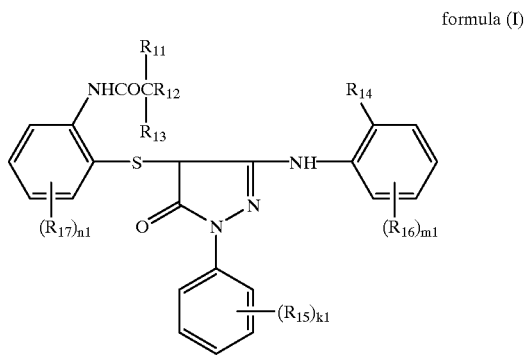

formula (I)

wherein $R_{11}$ represents a secondary or tertiary alkyl group, or a cycloalkyl group; $R_{12}$ represents an aryloxy group; $R_{13}$ represents a hydrogen atom, an alkyl group, a cycloalkyl group, an aryl group or a heterocyclic group; $R_{14}$ represents a halogen atom or an alkoxy group; $R_{15}$, $R_{16}$ and $R_{17}$ independently represent a substituent; k1 is an integer of 0 to 5; m1 and n1 are each an integer of 0 to 4;

(2) The silver halide color photographic material described in (1) above, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (II):

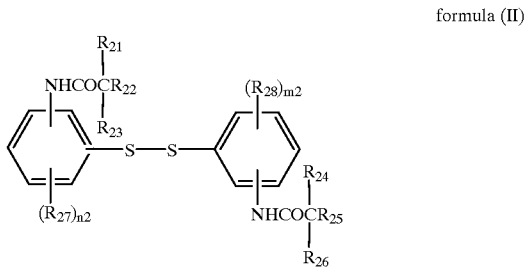

formula (II)

wherein $R_{21}$ and $R_{24}$ represent a secondary or tertiary alkyl group, or a cycloalkyl group; $R_{22}$ and $R_{25}$ represent an aryloxy group; $R_{23}$ and $R_{26}$ represent a hydrogen atom, an alkyl group, a cycloalkyl group, an aryl group or a heterocyclic group; $R_{27}$ and $R_{28}$ independently represent a substituent; m2 and n2 are each an integer of 0 to 4;

(3) The silver halide color photographic material described in (1) or (2) above, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (III):

formula (III)

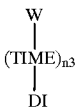

wherein W represents a coupler moiety capable of forming a dye capable of being leached out of the photographic material upon reaction with an oxidation product of a color developing agent; TIME represents a timing group capable of releasing an inhibitor residue DI after being released from W upon reaction with an oxidation product of a color developing agent; and n3 is an integer of 0, 1 and 2;

(4) The silver halide color photographic material described in (1) or (2) above, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (IV):

formula (IV)

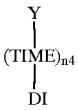

wherein Y represents an yellow coupler moiety capable of forming an yellow dye upon reaction with an oxidation product of a color developing agent; TIME represents a timing group capable of releasing an inhibitor residue DI after being released from Y upon reaction with an oxidation product of a color developing agent; and n4 is an integer of 0, 1 and 2;

(5) The silver halide color photographic material described in any one of (1) through (4) above, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (V):

formula (V)

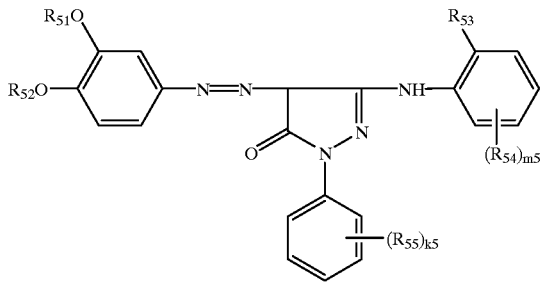

wherein $R_{51}$ and $R_{52}$ independently represent a secondary or tertiary alkyl group or a cycloalkyl group; $R_{53}$ represents a halogen atom or an alkoxy group; $R_{54}$ and $R_{55}$ independently represent a substituent; k5 is an integer of 0 to 5; and m5 is an integer of 0 to 4.

DETAILED DESCRIPTION OF THE INVENTION

The coupler (magenta coupler) represented by formula (I) will be described in detail.

In formula (I), $R_{11}$, represents a secondary or tertiary alkyl group (e.g., i-propyl, sec-butyl, t-butyl, t-amyl, etc.) or a cycloalkyl group (e.g., cyclopropyl, cyclopentyl, cyclohexyl, etc.). The group represented by $R_{11}$ may be substituted but unsubstituted one is preferred. The group represented by formula $R_{11}$ preferably has 3 to 12 carbon atoms, and more preferably 3 to 6 carbon atoms. Specifically preferred $R_{11}$ is a secondary alkyl group and iso-propyl group is still more preferred. $R_{12}$ represents an aryloxy group (e.g., phenoxy, naphthyloxy, etc.). The aryloxy group may be substituted by substituents and examples of the substituents include the following:

an alkyl group (e.g., t-amyl, t-octyl, dodcyl, etc), an cycloalkyl group (e.g., cyclopropyl, cyclhexyl, etc), an aryl (e.g., phenyl, naphthyl, etc), a heterocyclic group (e.g., 2-tetrahydrofuryl, 2-thiophenyl, 4-imidazolyl, indoline-1-yl, 2-pyridyl, etc), a carbonyl group (e.g., alkylcarbonyl such as acetyl, trifluoroacetyl and pivaloyl, and arylcarbonyl such as benzoyl, pentafluorobenzoyl and 3,5-di-t-butyl-4-hydroxybenzoyl), an oxycarbonyl group (e.g., alkoxycarbonyl such as methoxycarbonyl, cyclohexyloxycarbonyl and dedecyloxycarbonyl, aryloxycarbonyl such as phenoxycarbonyl, 2,4-di-t-amylphenoxycarbonyl and 1-naphthyloxycarbonyl, and heterocyclic-oxycarbonyl such as 2-pyridyloxycarbonyl and 1-phenylpyrazolyl-5-oxycarbonyl), a carbamoyl group (e.g., alkylcarbamoyl such as dimethylcarbamoyl and 4-(2,4-di-t-amylphenoxy)butylcarbonyl, and arylcarbamoyl such as 1-naphthylcarbamoyl), a sulfonyl group (e.g., alkylsulfonyl such as methanesulfonyl and trifluoromethanesulfonyl, and arylsulfonyl such as p-toluenesulfonyl), a sulfamoyl (e.g., alkylsulfamoyl such as dimethylsulfamoyl and 4-(2,4-di-t-amylphenoxy)butylaminosulfonyl, and arylsulfamoyl such as phenylsulfamoyl), a halogen atom, cyano group, nitro group, an alkenyl group (e.g., 2-propylene, oleyl, etc), hydroxy group, an alkoxy group (e.g., methoxy, 2-ethoxyethoxy, etc)an aryloxy group (e.g., phenoxy, 2,4-di-t-amylphenoxy, 4-(4-hydroxyphenylsulfonyl)phenoxy, etc), a heterocyclic-oxy group (e.g., 4-pyridyloxy, 2-hexahydropiranyloxy, etc), a carbonyloxy group (e.g., alkylcarbonyloxy such as acetyloxy, trifluoroacetyloxy and pivaloyloxy, and aryoxy such as benzoyloxy and pentfluorobenzoyloxy)a urethane group (e.g., alkylurethane such as N,N-dimethylurethane and arylurethane such as N-phenylurethane, N-(p-cyanophenyl)urethane), a sulfonyloxy group (e.g., alkylsulfonyoxy such as methanesulfonyloxy, trifluoromethanesulfonyloxy and dodecanesulfonyloxy and arylsulfonyloxy such as benzenesulfonyloxy and p-toluenesulfonyloxy), an amino group (e.g., alkylamino such as dimethylamino, cyclohexylamino and dodecylamino, and arylamino such as anilino and p-t-octylanilino), a sulfonylamino group (e.g., alkylsulfonylamino such as methanesulfonylamino, heptafluoropropanesulfonylamino and hexadecysulfonylamino, and arylsulfonylamino such as p-toluenesulfonylamino and pentafluorobenzenesulfonylamino), a sulfamoylamino group (e.g., alkylsulfamoylamino such as N,N-dimethylsulfamoylamino and arylsulfamoylamino such as N-phenylsulfamoylamino), an acylamino group (e.g., alkylcarbonylamino such as acetylamino and myrystylamino and arylcarbonylamino such as benzoylamino), a ureido group (e.g., alkylureido such as N,N-dimethylureido, and arylureido such as N-phenylureido and N-(p-cyanophenyl)ureido), an alkylthio group (e.g., methylthio, t-octylthio, etc), an arylthio group (e.g., phenylthio, etc), and a heterocycli-thio group (e.g., 1-phenyltetrazole-5-thio, 5-methyl-1,3,4-oxazole-2-thio, etc).

Of the groups represented by $R_{12}$ is preferred a phenoxy group having a substituent on the benzene ring, i.e., a substituted phenoxy. The substituent is preferably an alkyl group, a cycloalkyl group, an alkoxy group, a halogen atom and an alkoxycarbonyl group. The total carbon number of the substituent(s) on the benzene ring is preferably 4 to 20 and more preferably 8 to 12.

$R_{13}$ represents a hydrogen atom, a cycloalkyl group, an aryl-group or a heterocyclic group, of which a hydrogen atom is preferred. $R_{14}$ represents a halogen atom (e.g., chlorine, bromine, iodine, etc.) or a alkoxy group (e.g., methoxy, I-propoxy, etc.), of which $R_{14}$ is preferably a chlorine atom or methoxy group. $R_{15}$ represents a substituent. Any group capable of being substituted on a benzene ring may be included and exemplary examples thereof are the same as cited as the substituents for $R_{12}$. $R_{15}$ is prefrerably a halogen atom and a chlorine atom is specifically preferred. Specifically, three chlorine atoms being substituted at the 2, 4, 6-position is preferred.

$R_{16}$ also represents a substituent. Any group capable of being substituted on a benzene ring may be included and exemplary examples thereof are the same as cited as the substituents for $R_{12}$. $R_{16}$ is preferably an acylamino group, an oxycarbonyl group, carbamoyl group, sulfonyl group and sulfamoyl group. $R_{17}$ also represents a substituent. Any group capable of being substituted on a benzene ring may be included and exemplary examples thereof are the same as cited as the substituents for $R_{12}$. $R_{15}$ is prefrerably a halogen atom.

Representative examples of the coupler represented by formula (I) are shown below but are not limited to these examples.

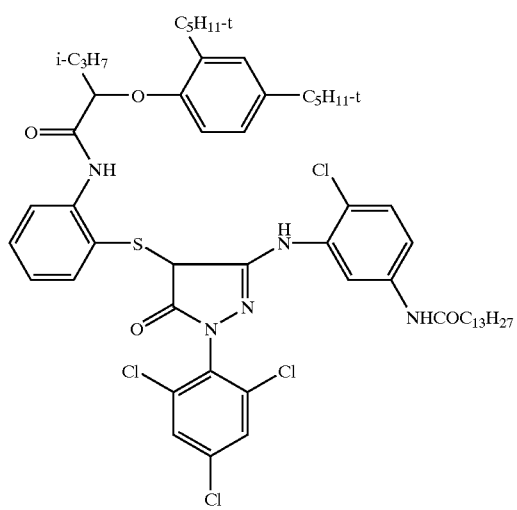

I-1

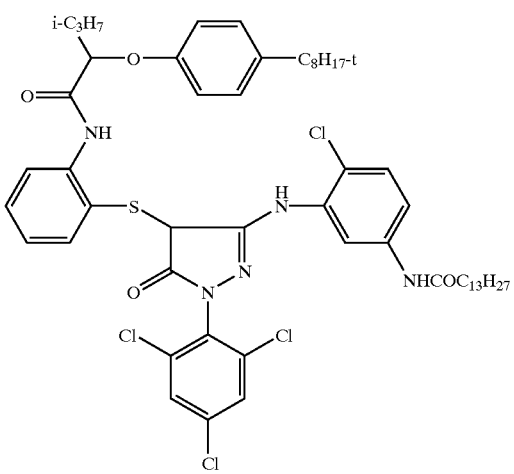

I-2

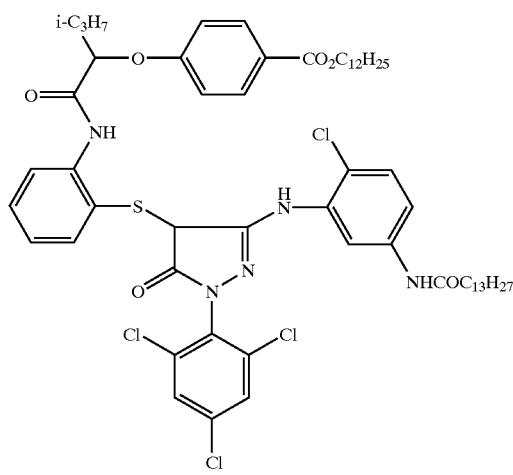

I-3

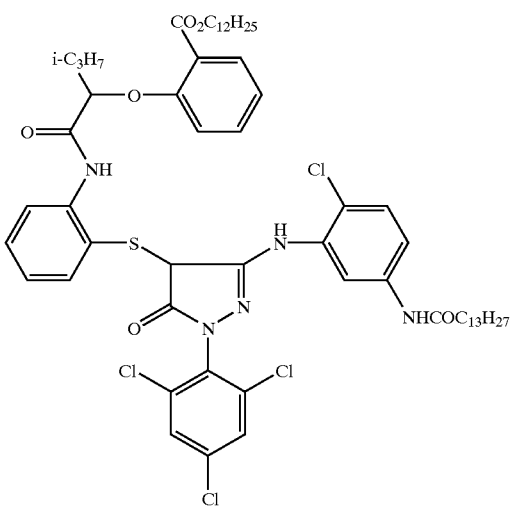

I-4

-continued
I-5
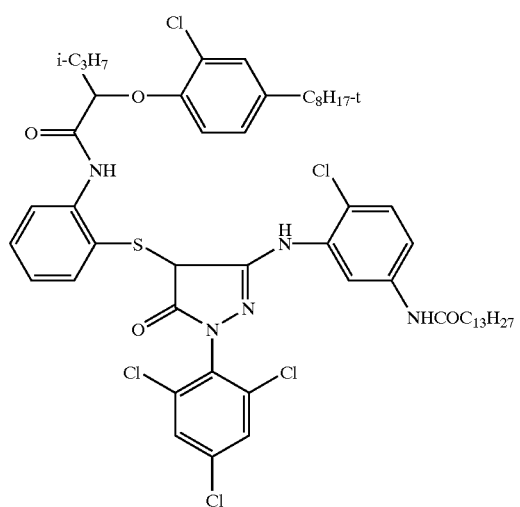
I-6
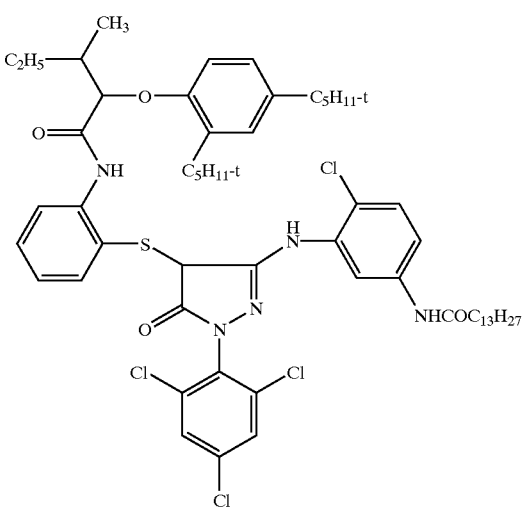
I-7
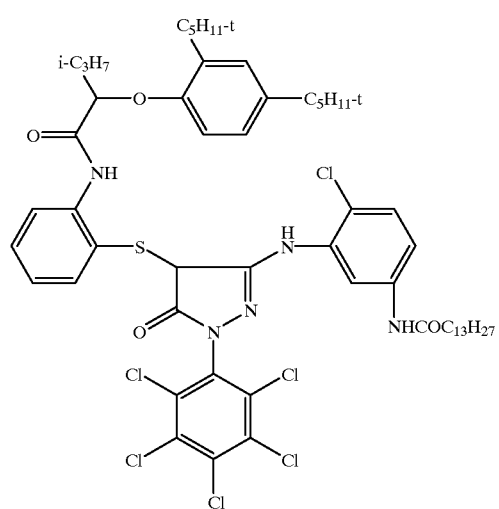
I-8
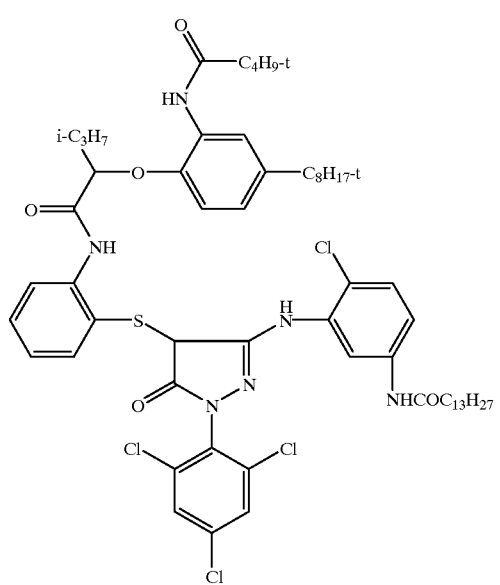
I-9
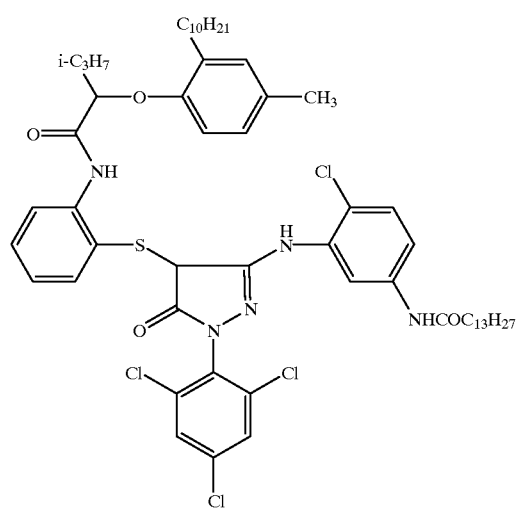
I-10
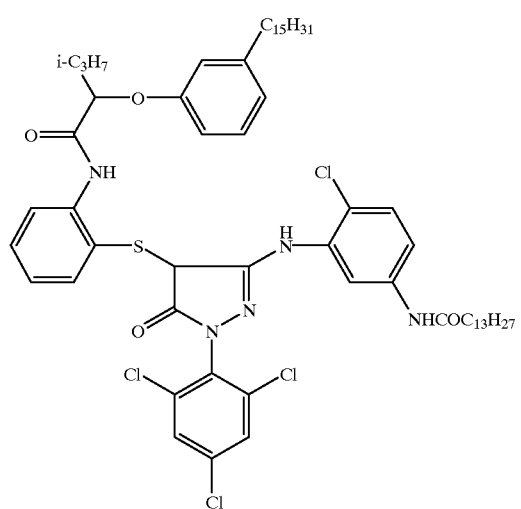

-continued
I-11
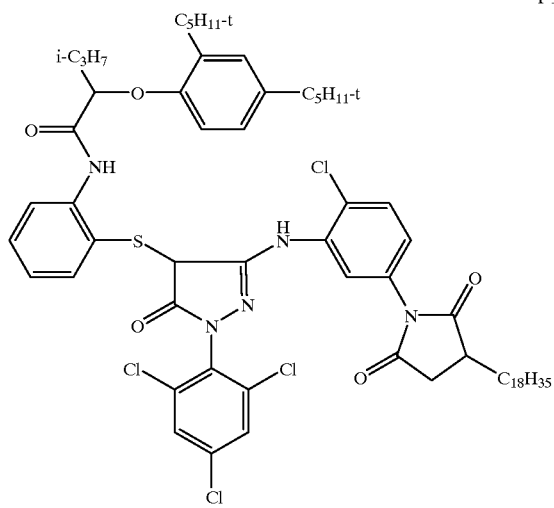
I-12
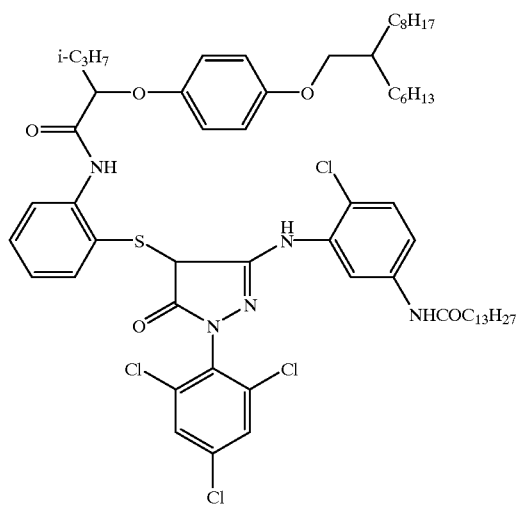
I-13
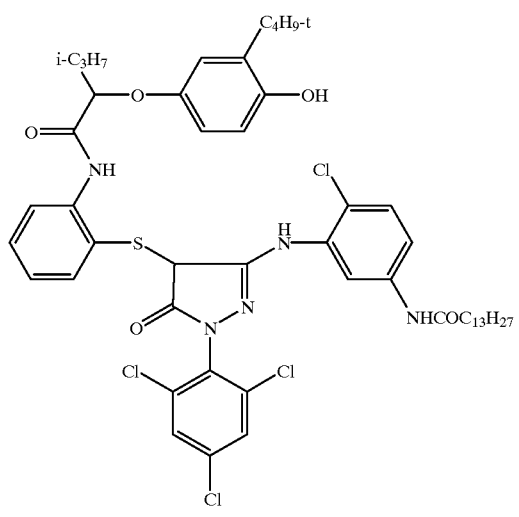
I-14
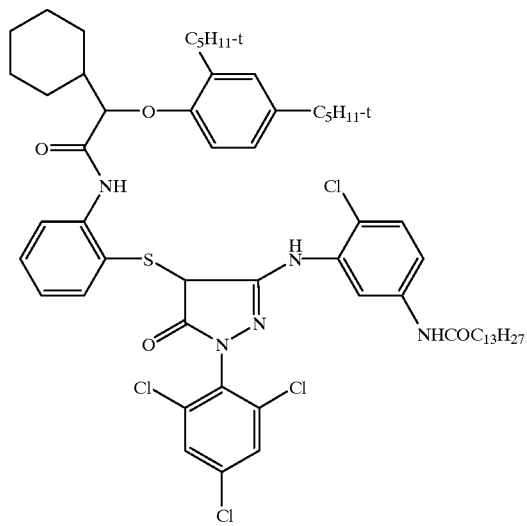
I-15
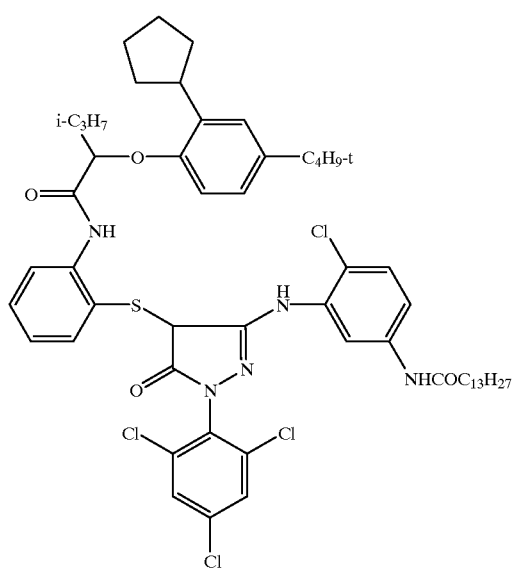

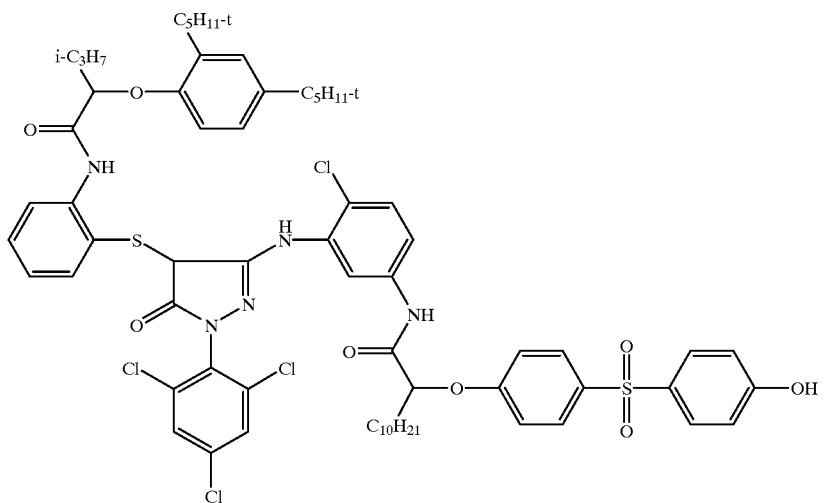
I-16
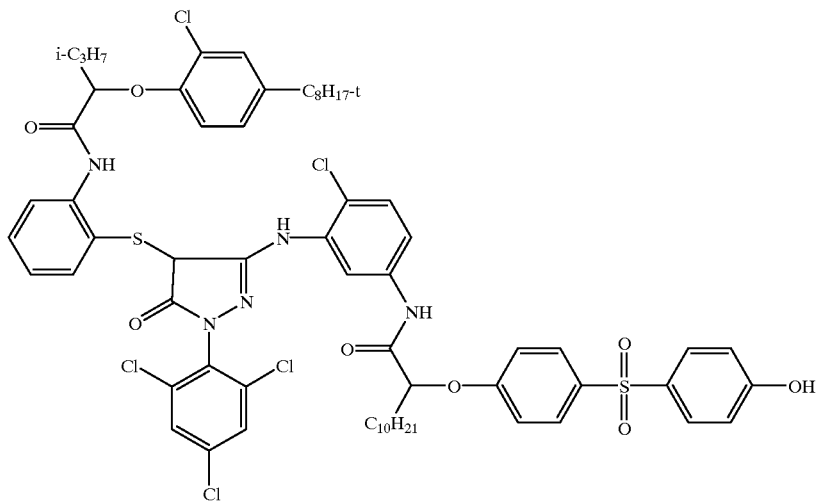
I-17
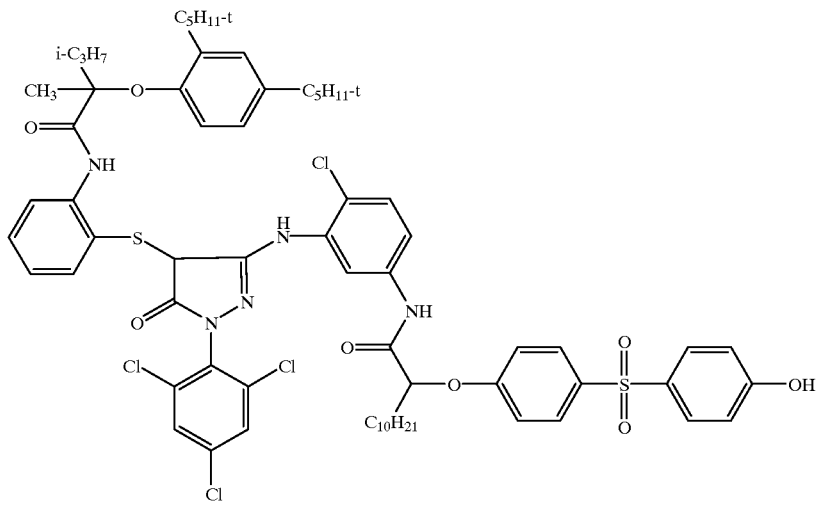
I-18

-continued
I-19
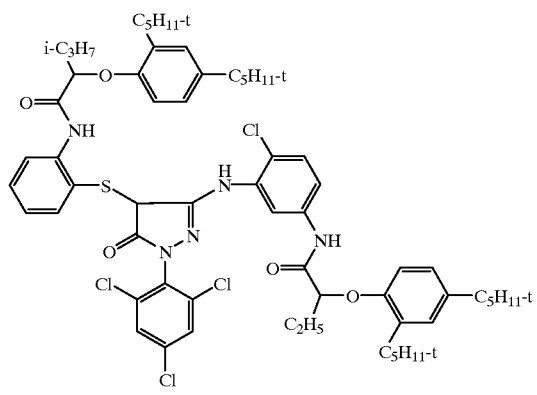
I-20
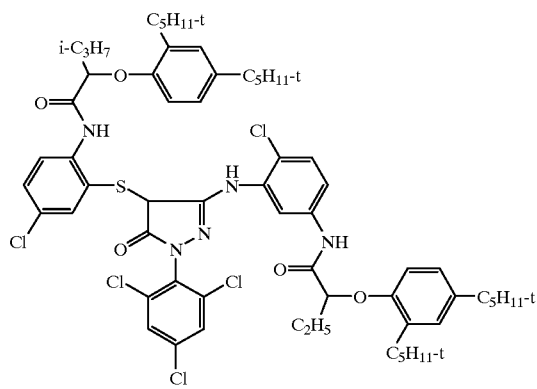
I-21
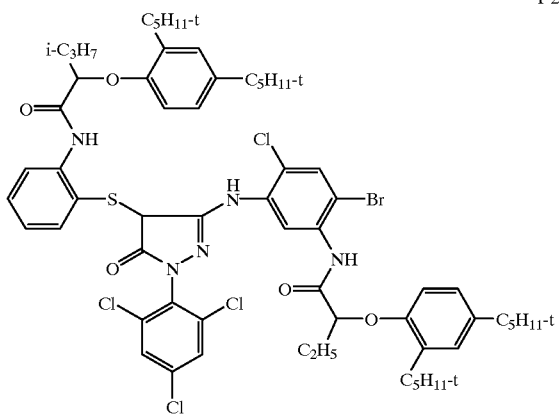
I-22
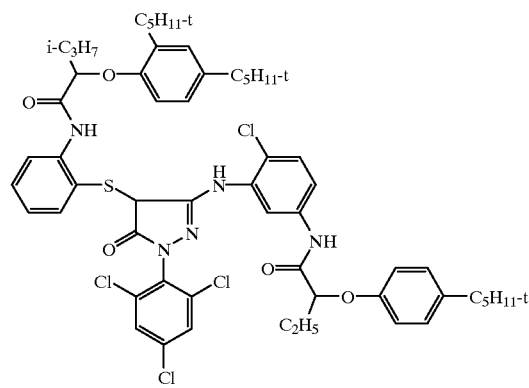
I-23
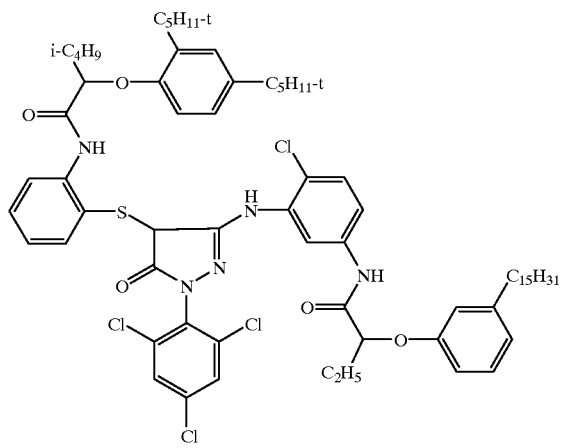
I-24
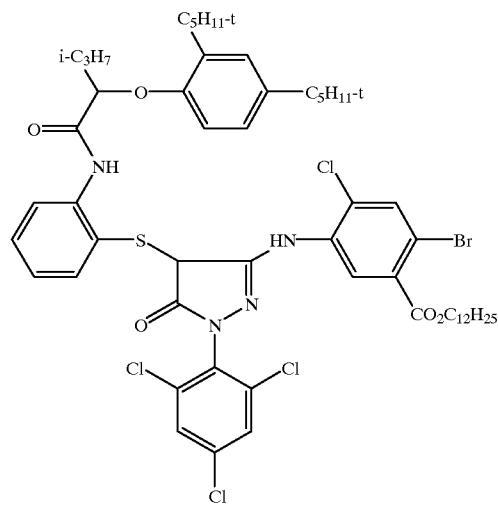

I-25
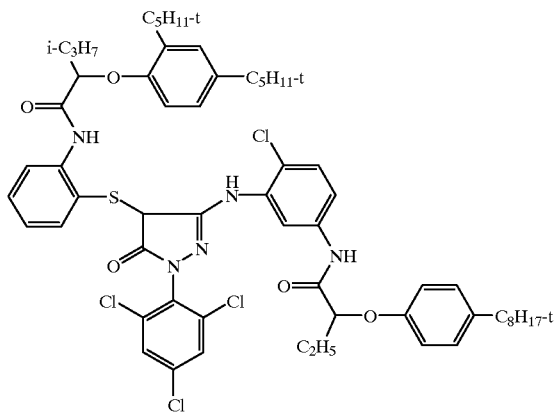
I-26
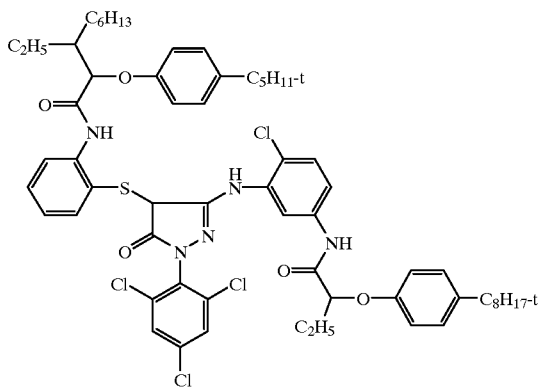
I-27
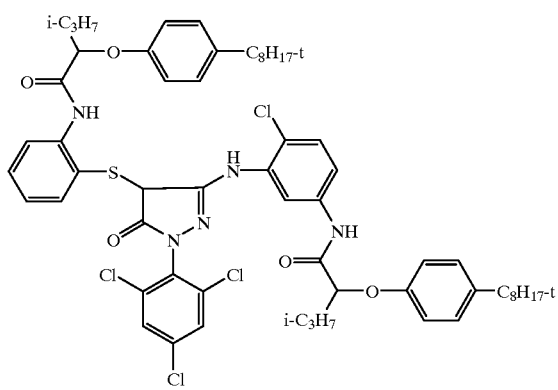
I-28
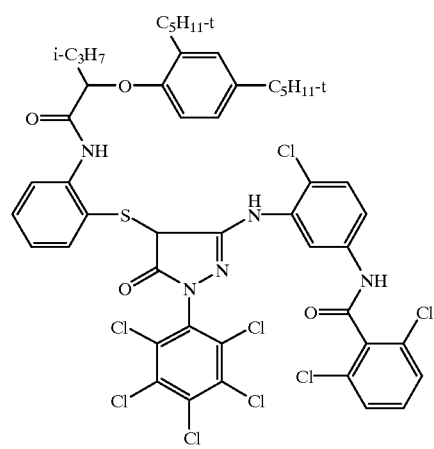
I-29
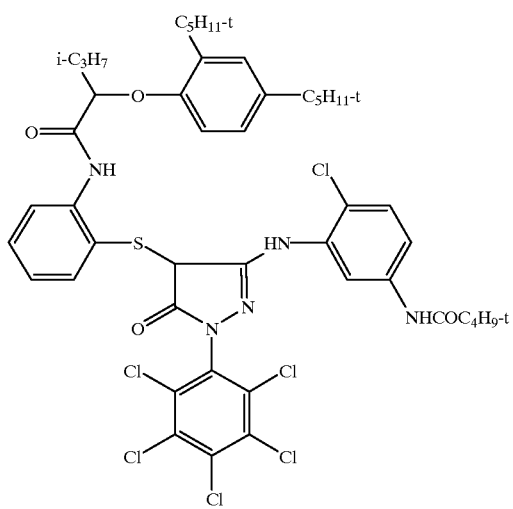
I-30
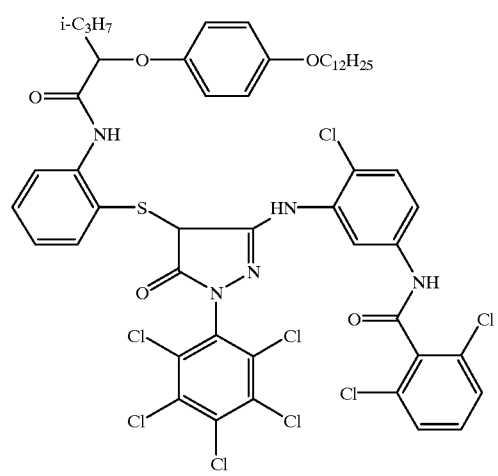

-continued
I-31
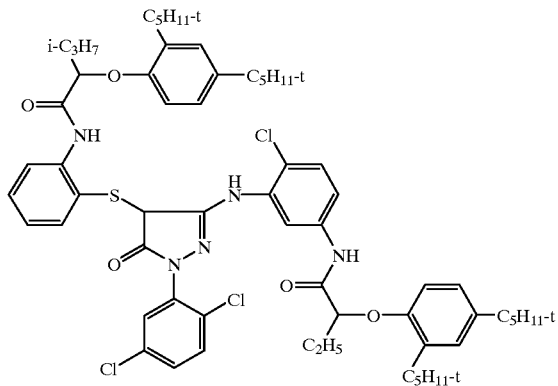
I-32
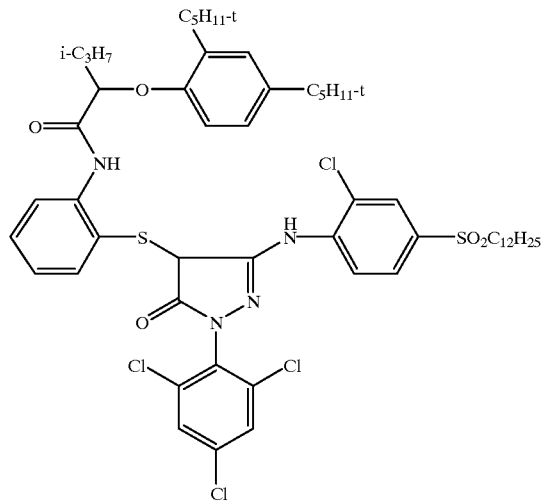
I-33
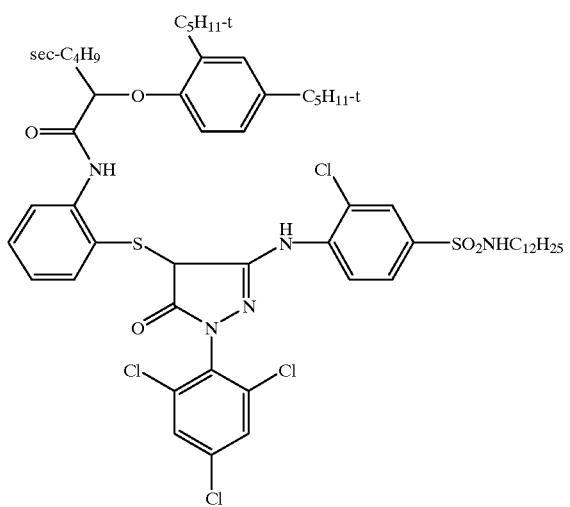
I-34
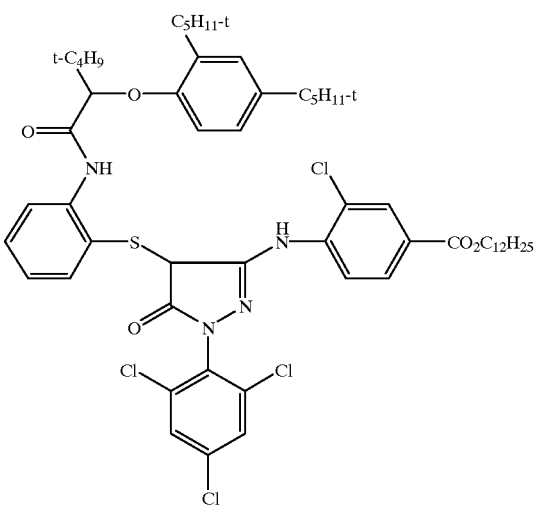
I-35
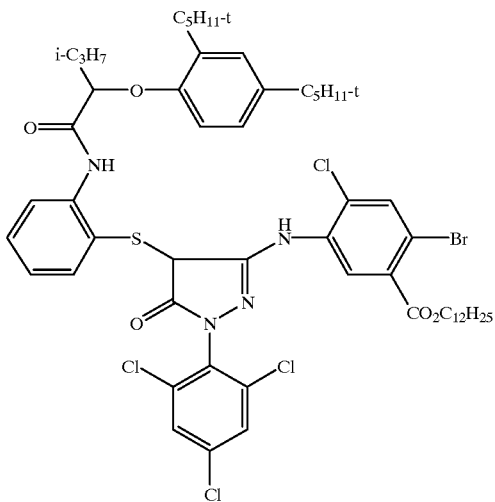
I-36
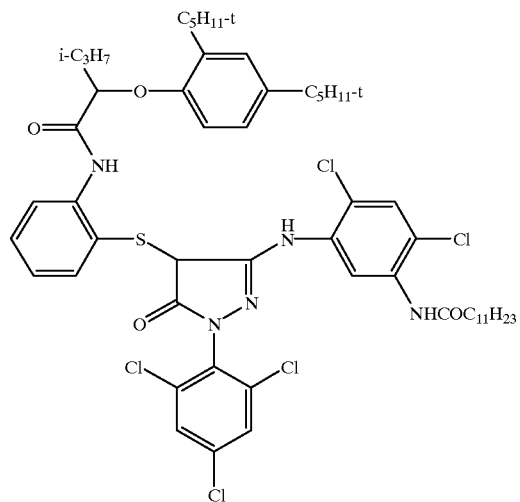

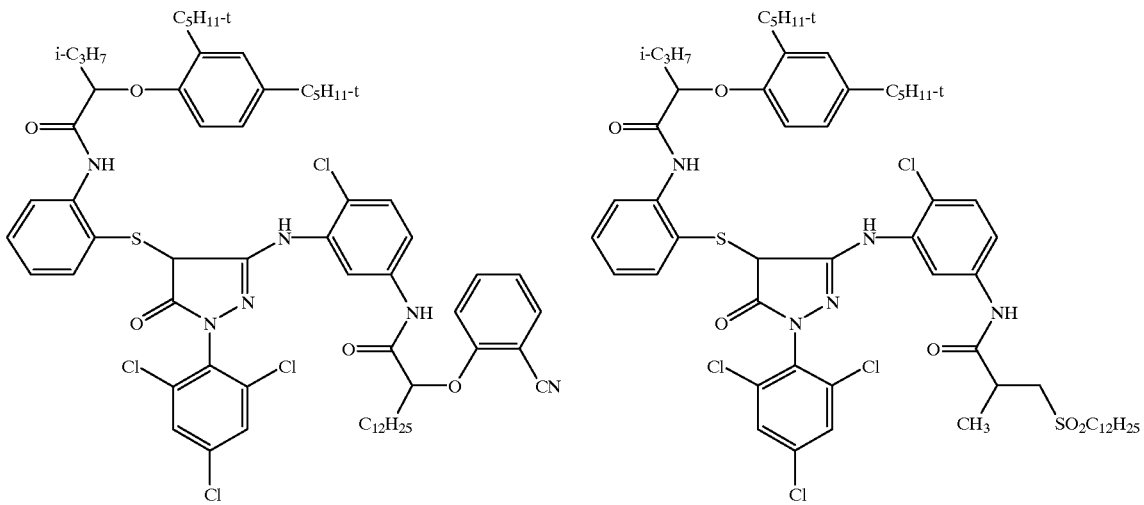

I-37

I-38

The compound represented by formula (II) will be described. In formula (II), $R_{21}$ and $R_{24}$ independently represent a secondary or tertiary alkyl group or a cycloalkyl group and exemplary examples thereof are the same as cited as $R_{11}$ of formula (I). $R_{22}$ and $R_{25}$ each represent an aryloxy group and exemplary examples thereof are the same as cited as $R_{12}$ of formula (I). $R_{23}$ and $R_{26}$ each represent a hydrogen atom, an alkyl group, a cycloalkyl group, an aryl group or a heterocyclic group, and exemplary examples thereof are the same as cited as $R_{13}$ of formula (I). $R_{27}$ and $R_{28}$ each represent a substituent and exemplary examples thereof are the same as cited as $R_{17}$ of formula (I). In formula (II), two —NHCO groups may be substituted on any position of each benzene ring and substitution at the ortho-position for the sulfur atom is preferred.

Representative examples of the compound represented by formula (II) are shown below, but are by no means limited to these examples.

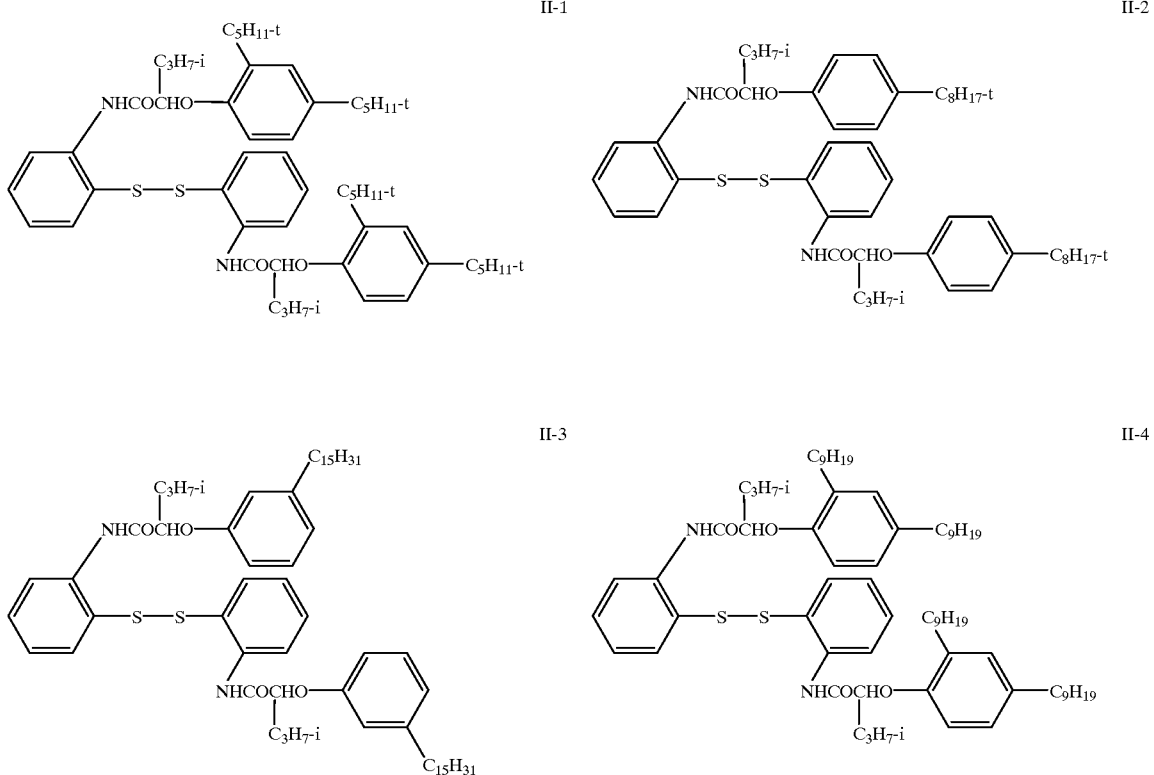

II-1

II-2

II-3

II-4

-continued
II-5
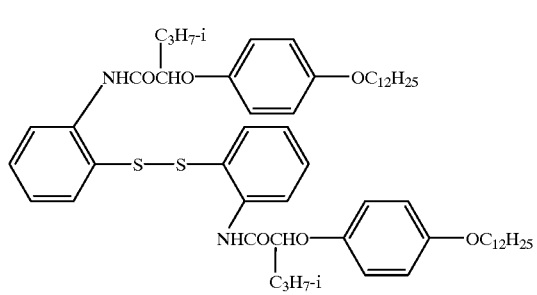
II-6
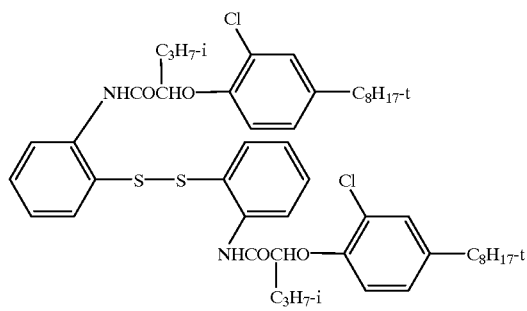
II-7
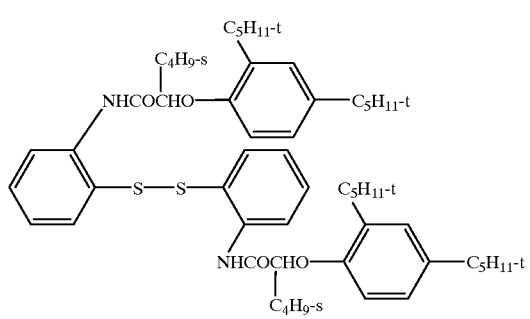
II-8
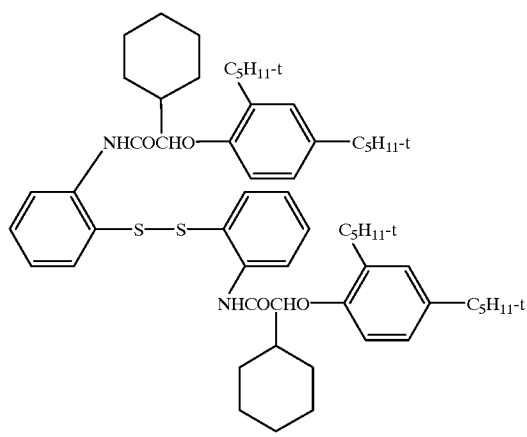
II-9
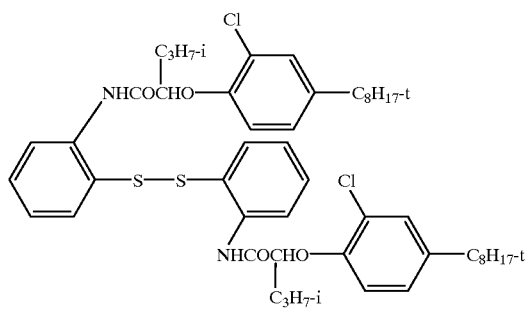
II-10
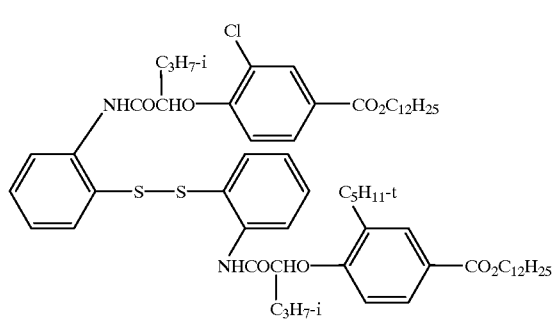
II-11
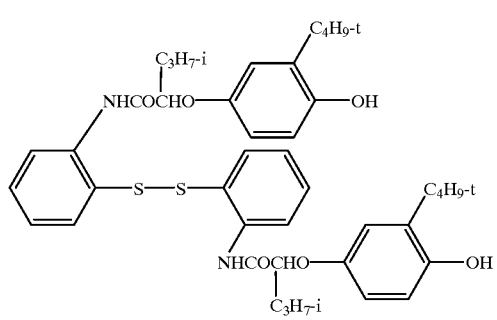

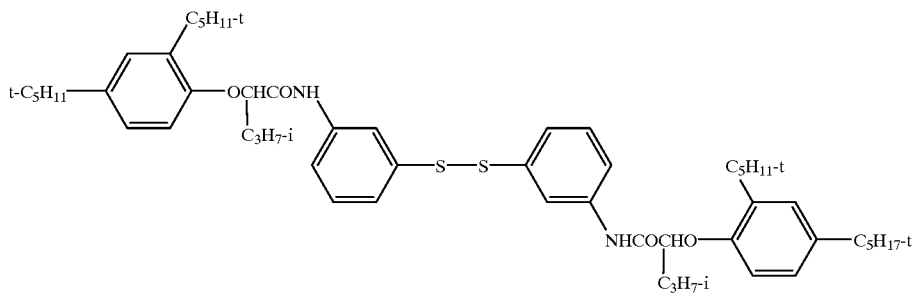
II-12
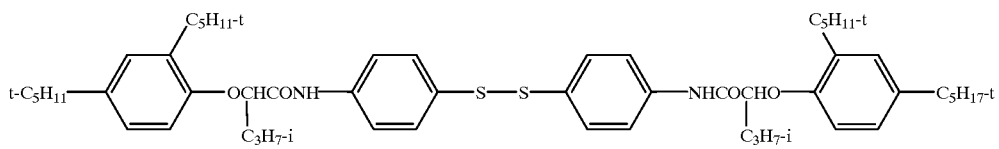
II-13
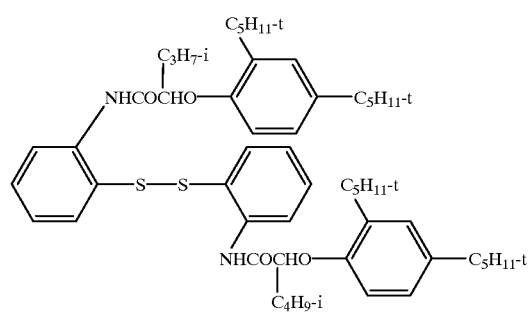
II-14
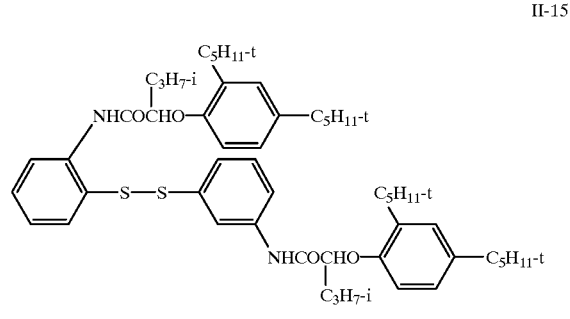
II-15
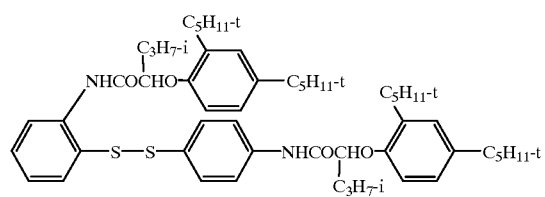
II-16
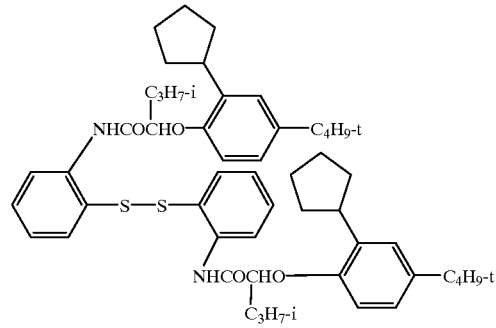
II-17
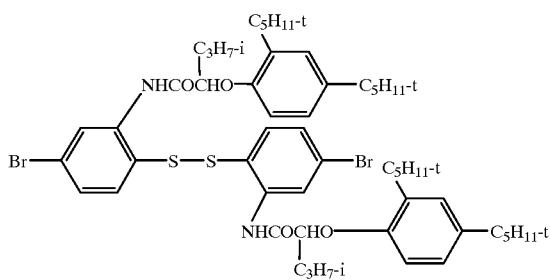
II-18

-continued

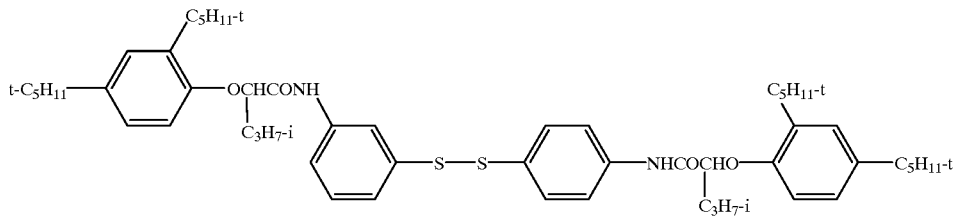

II-19

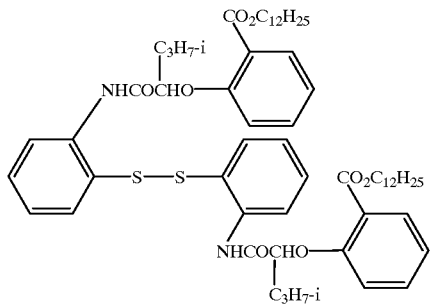

II-20

Next, the compound represented by formula (III) will be described. The compounds represented by formula (III) are a so-called leachable decoloring DIR coupler, as described in JP-A Nos. 58-160954, 63-37350, 4-356042, 5-61160 (hereinafter, the term, JP-A means an unexamined published Japanese Patent Application); and U.S. Pat. No. 4,482,629.

In formula (III), the coupler moiety represented by W may be any coupler moiety having the same property as described above, and is preferably a 1-naphthol substituted at the 2-position by an unsubstituted carbamoyl group or an alkylcarbamoyl group substituted with a water-solubilizing group (e.g., carboxy, sulfo, hydroxy, methoxycarbonyl, ethoxycarbonyl, etc.), in terms of higher reactivity and superior leachability.

The group represented by TIME is a so-called timing group and a linkage group used for the purpose of adjustment of the coupling reaction rate of the compound of formula (III) and an oxidation product of a color developing agent, and of the releasing rate of the inhibitor residue represented by DI. Representative timing groups are described in U.S. Pat. Nos. 4,861,701, 4,248,962, 4,409,323, 4,482,629 and 4,857,447.

The inhibitor residue represented by DI refers to a compound having a function of retarding the developing rate in the color developing process, that is, a group in which a hydrogen atom is removed from the inhibitor. Exemplary inhibitors include mercaptotetrazoles, mercaptobenzothiazoles, mercaptobenzoxazoles, mercaptobenzimidazoles, mercpatooxadiazoles, mercaptothiadiazoles, benzoriazoles, and 1,2,3- or 1,2,4-triazoles. From the viewpoint of reduction in contamination of processing solutions, the DI is preferably a compound inhibiting development at the time of being released from the active position of the coupler upon color development reaction, which is decomposed to a compound substantially having no photographic effect, after being leached into a color developing solution. The compound releasing the DI exhibiting such properties is a so-called deactivation type DIR coupler. The deactivation type DIR coupler is systematically defined in JP-A 57-151944, and exemplary compounds are described in JP-A Nos. 58-205150, 60-218644, 60-221750, 60-233650, 61-11743, 2-48655, 3-18844, 3-228048, 4-211245, 4-308842; and U.S. Pat. No. 4,782,012.

The compounds represented by formula (III) can be synthesized with reference to the methods described in the above-cited patents. Exemplary examples of the compound of formula (III) are shown below, but are by no means limited to these examples.

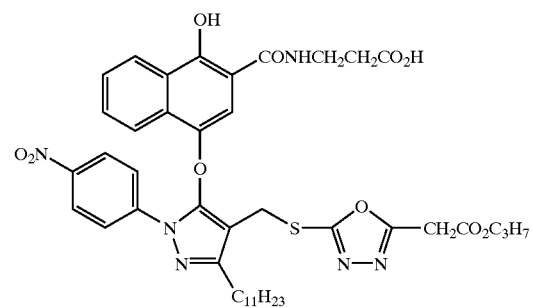

III-1

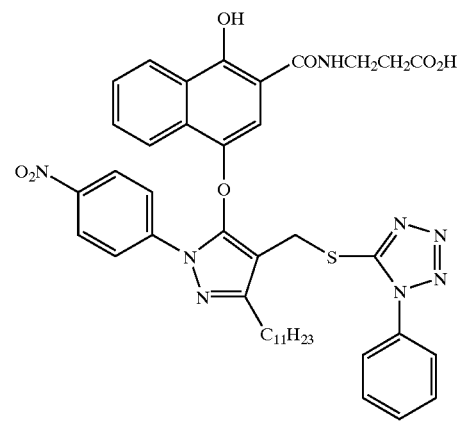

III-2

-continued
III-3
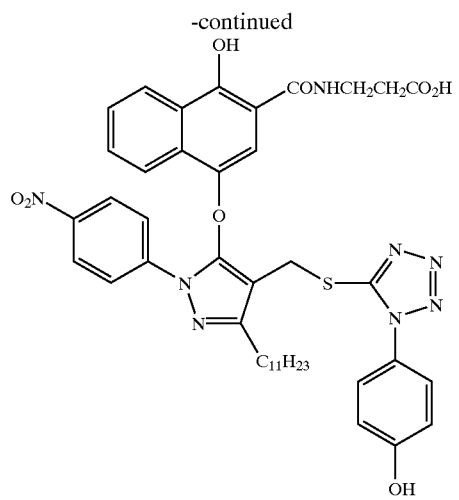
III-4
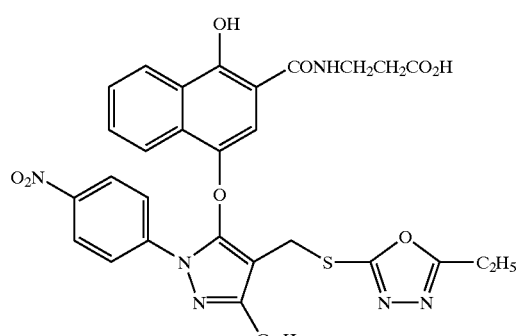
III-5
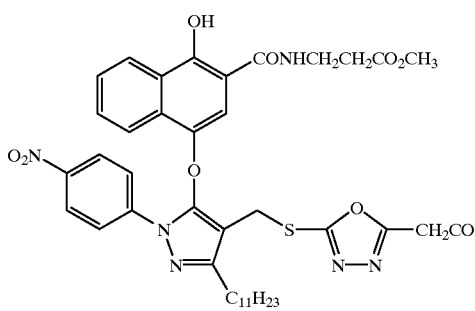
III-6
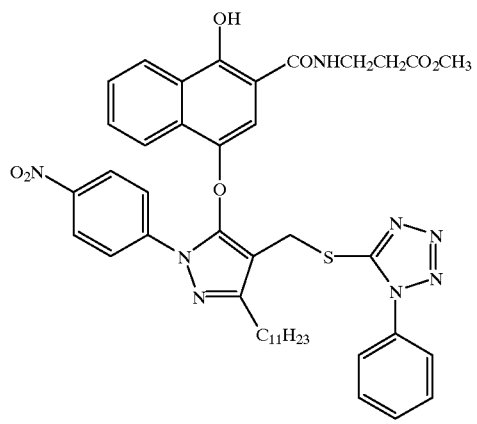
-continued
III-7
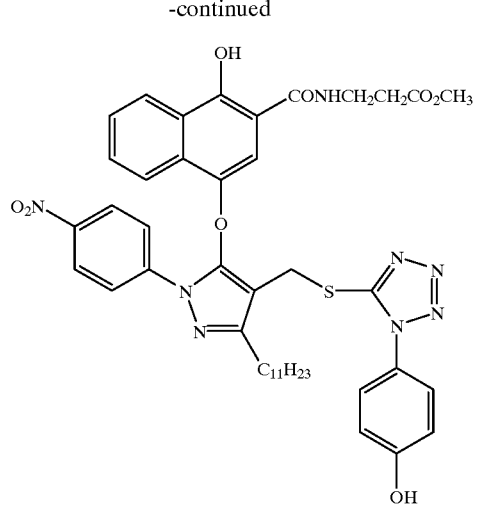
III-8
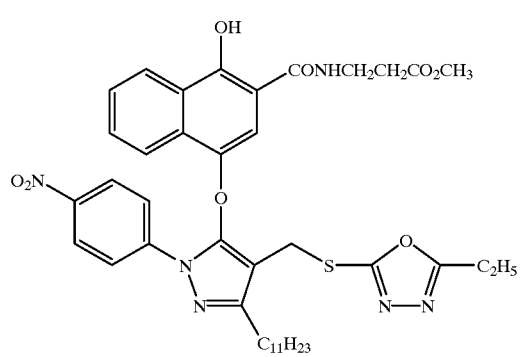
III-9
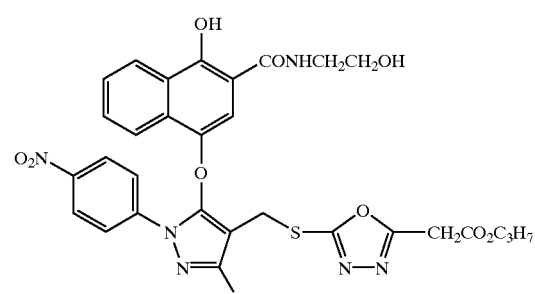
III-10
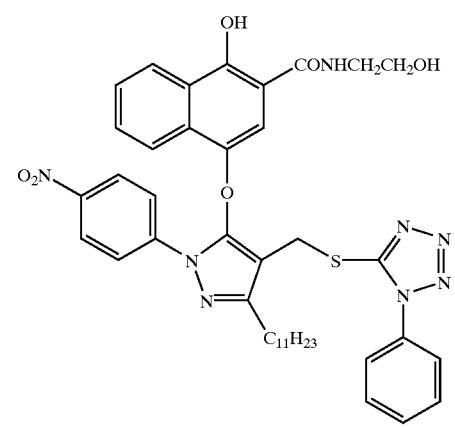

III-11
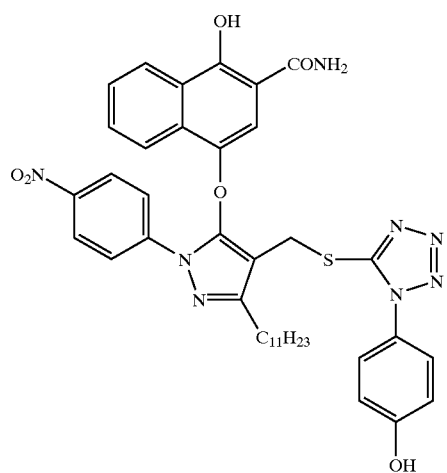
III-14
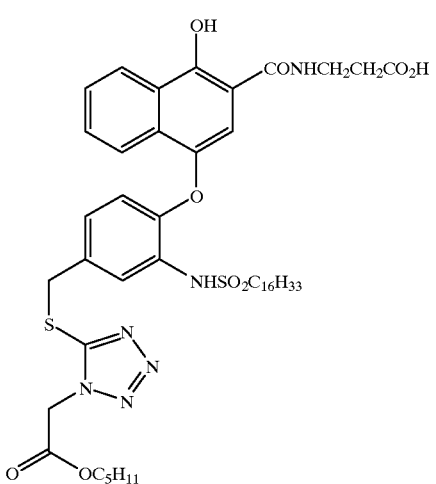
III-12
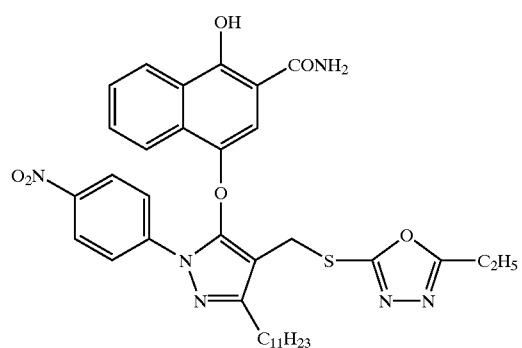
III-15
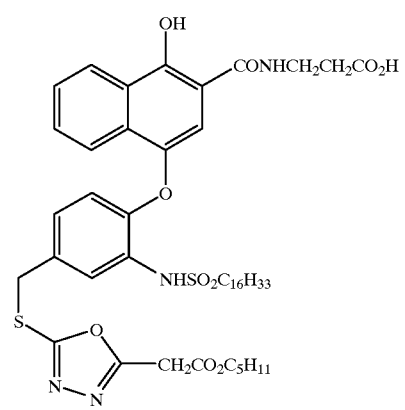
III-13
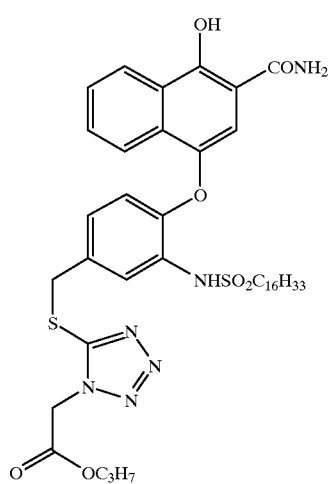
III-16
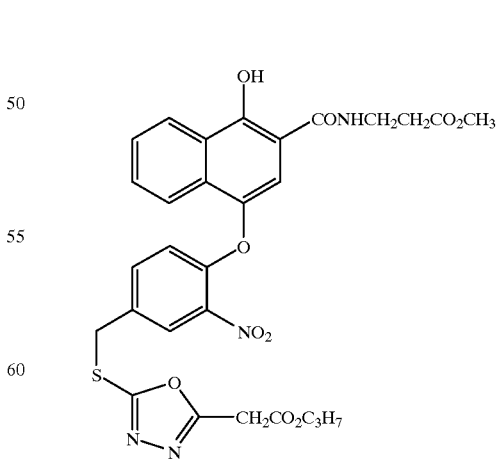

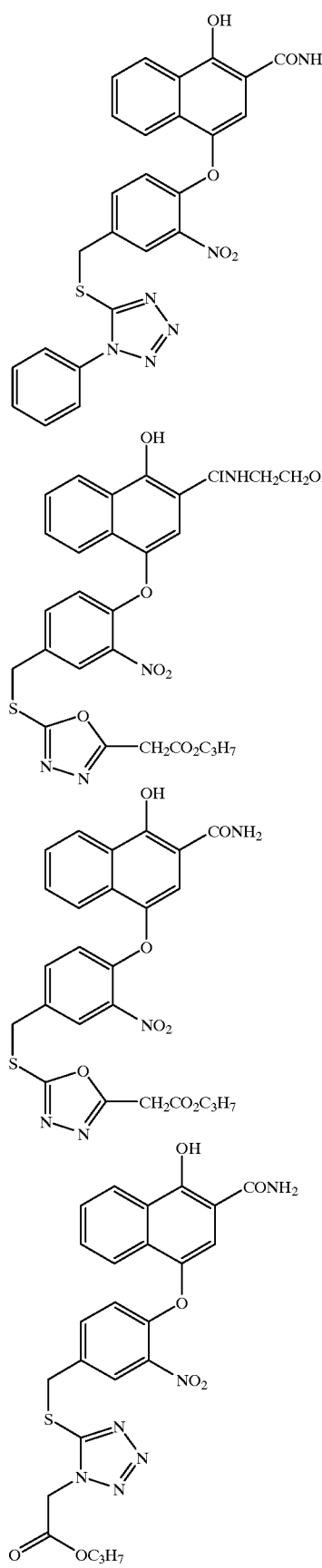
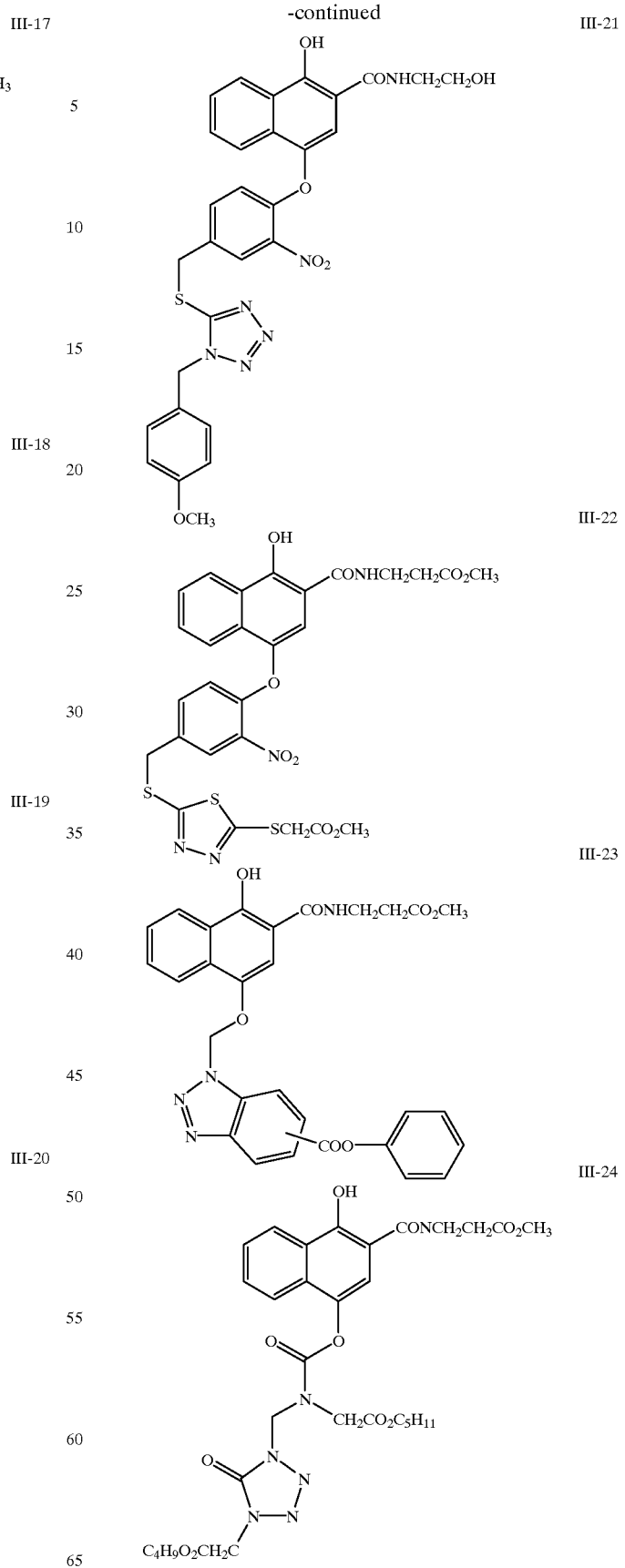
The compound represented by formula )IV) will be described below. In formula (IV), Y represents a coupler moiety capable of forming a yellow dye upon reaction with an oxidation product of a color developing agent in the color development process. Representative yellow dye forming couplers are described in U.S. Pat. Nos. 2,875,057, 2,407,210, 3,265,506, 2,298,433, 3,048,194, 3,447,928; and "Farbkuppler eine Literturiebersicht" (Affa Mitteilungen, Vol. III page 112-126, 1961). Preferred Y is acyacetoamides such as pivaloylacetoanilides and benzoylacetoanilides. TIME represent a timing group capable of releasing the DI after being released from Y upon reaction with an oxidation product of a color developing agent, and examples thereof are the same as cited as TIME and DI of formula (III).

The compounds represented by formula (IV) can be synthesized with reference to the methods described in the above-cited patents. Exemplary examples of the compound of formula (IV) are shown below, but are by no means limited to these examples.

IV-1

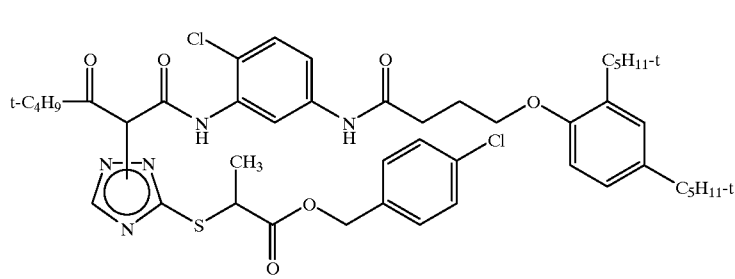

IV-2

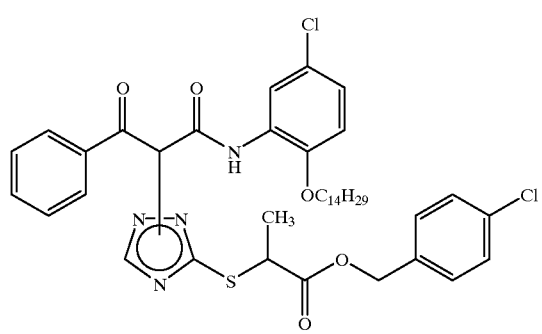

IV-3

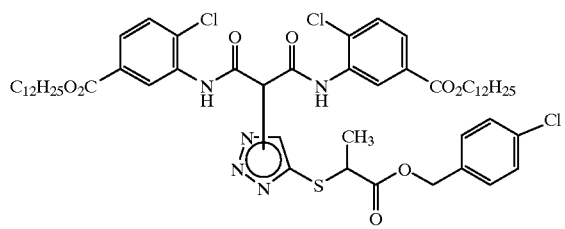

IV-4

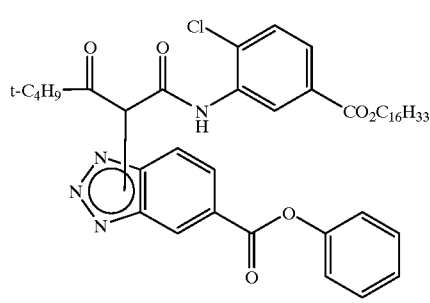

IV-5

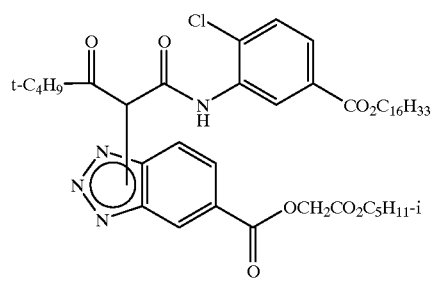

IV-6

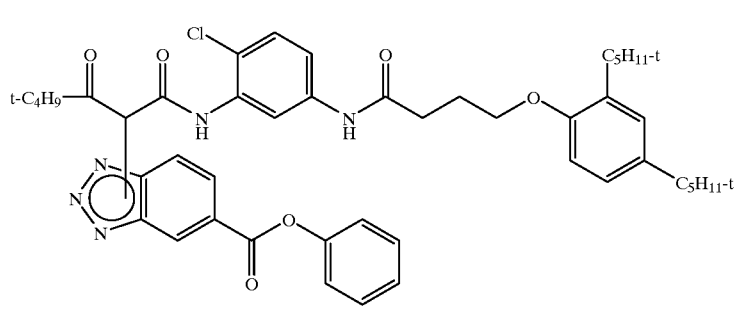

IV-7
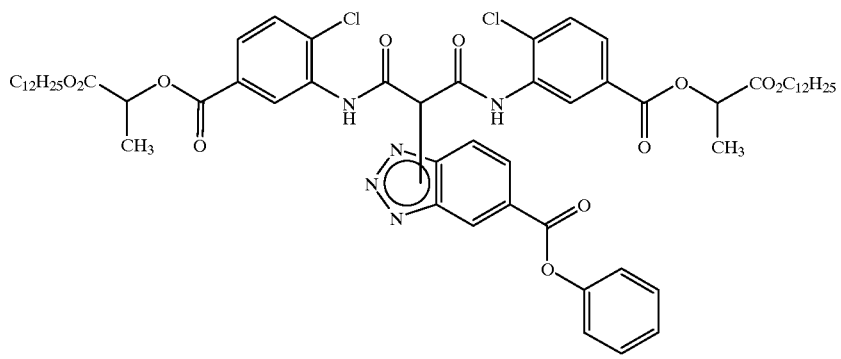
IV-8 IV-9
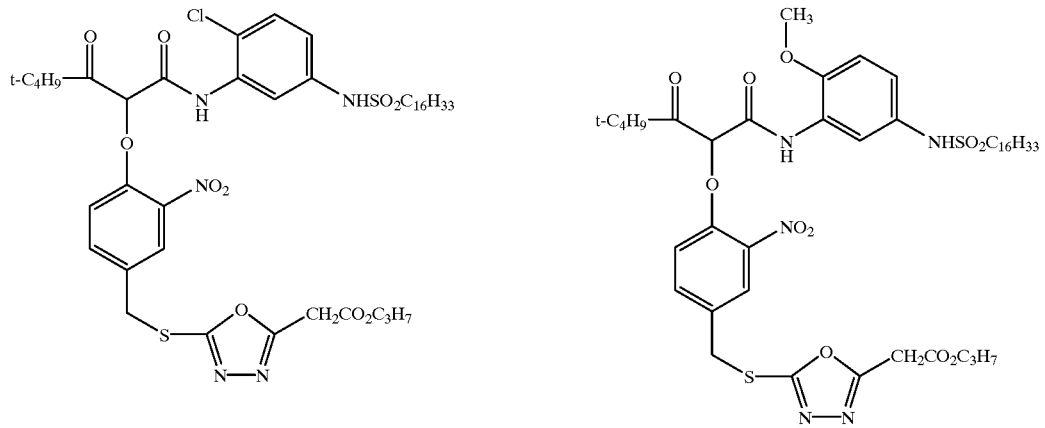
IV-10 IV-11
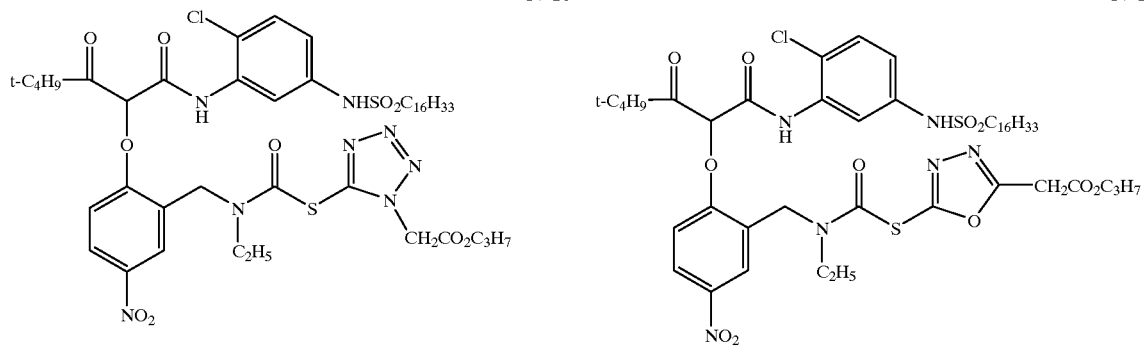
IV-12
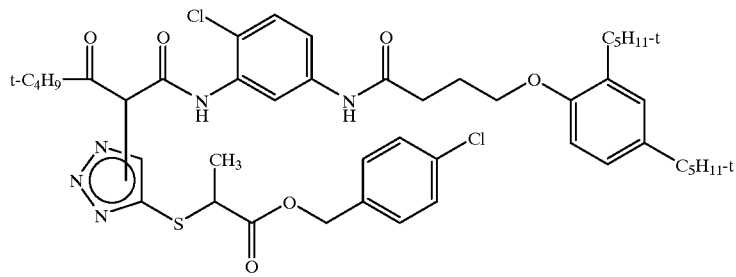

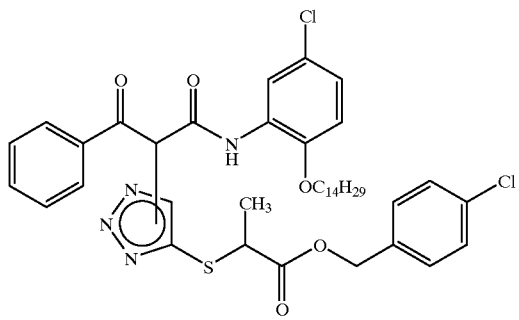
IV-13
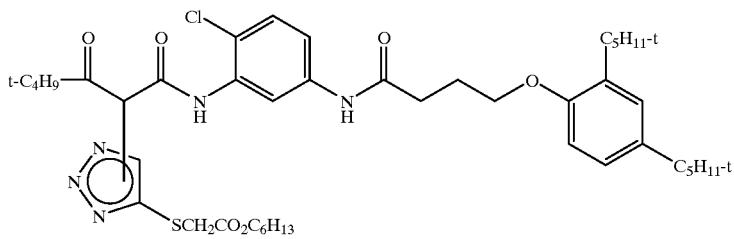
IV-14
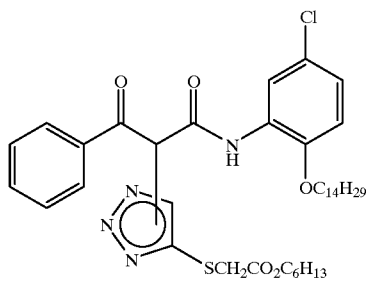
IV-15
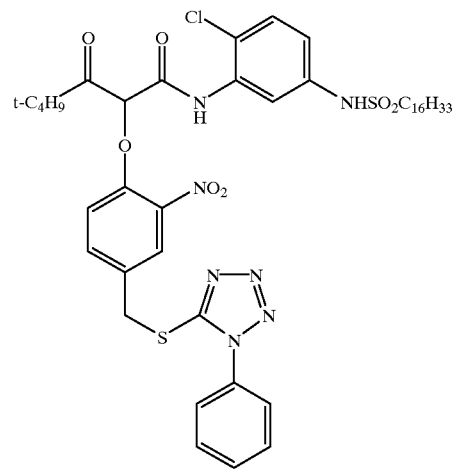
IV-16
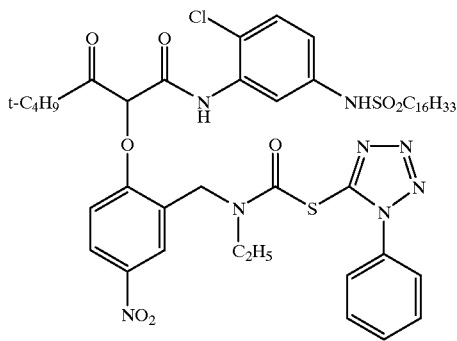
IV-17
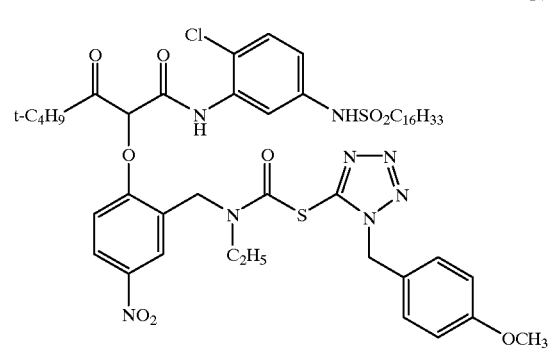
IV-18

IV-19

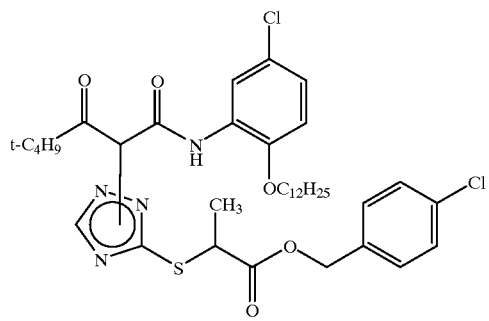

IV-20

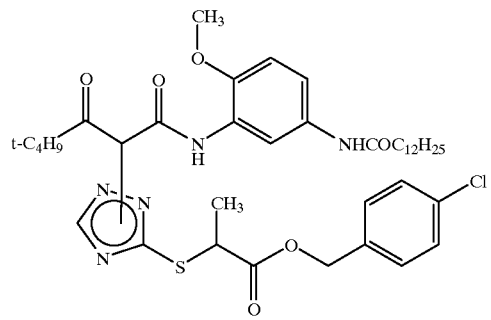

IV-21

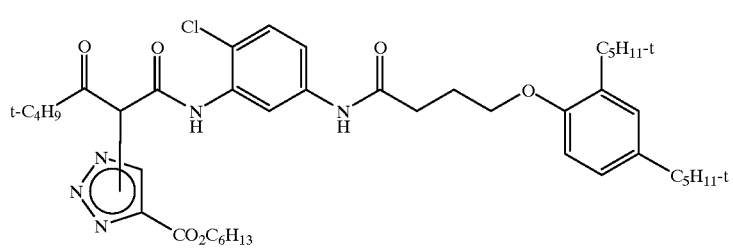

The compound represented by formula (V) will be described below. The compound represented by formula (V) is a so-called masking coupler or colored coupler, which is yellow-colored.

In formula (V), $R_{51}$ and $R_{52}$ represent a secondary or tertiary alkyl group (e.g., i0propyl, sec-butyl, t-butyl, t-amyl, etc.) or a cycloalkyl group (e.g., cyclopropyl, cyclopentyl, cyclohexyl, etc.). $R_{51}$ and $R_{52}$ is preferably a secondary or tertiary alky group having 6 or less carbon atoms or a cycloalkyl group, and i-propyl or sec-butyl are specifically preferred. $R_{53}$ represents a halogen atom (e.g., chlorine, fluorine, etc.) or an alkoxy group (e.g., methoxy, I-propoxy, etc.). $R_{53}$ is preferably a chlorine atom or methoxy group. $R_{54}$ represents a substituent. The substituent may be any group capable of being substituted on a benzene ring and examples thereof are the same as cited as substituent for $R_{12}$ of formula (I). $R_{54}$ is preferably an acylamino group, an oxycarbonyl group, a carbamoyl group, a sulfonyl group or a sulfamoyl group. $R_{55}$ also represents a substituent. The substituent may be any group capable of being substituted on a benzene ring and examples thereof are the same as cited as substituent for $R_{12}$ of formula (I). $R_{55}$ is preferably a halogen atom.

The compounds represented by formula (V) can be synthesized with reference to the method described in JP-A 62-50830. Exemplary examples of the compound of formula (V) are shown below but are by no means limited to these examples.

V-1

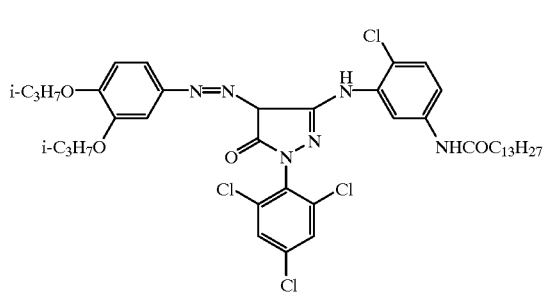

V-2

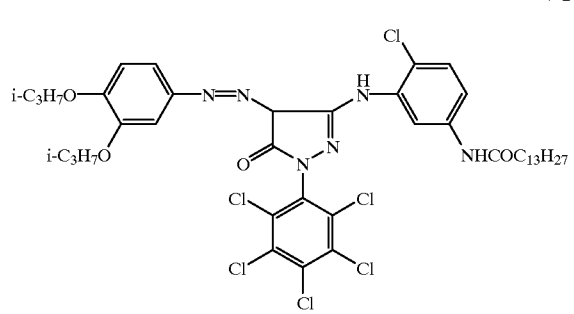

V-3
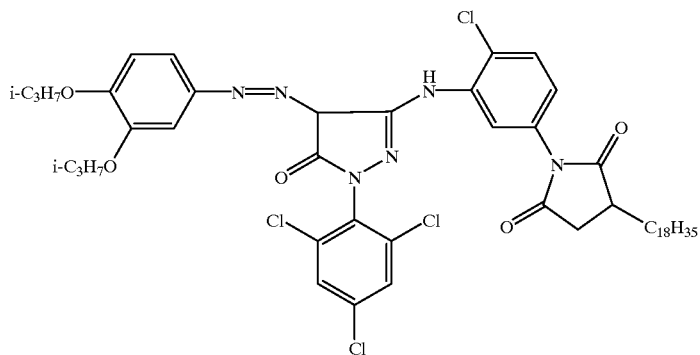
V-4
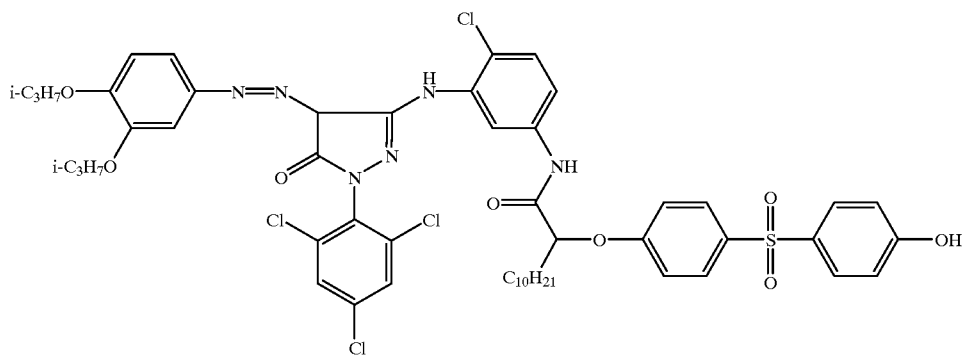
V-5
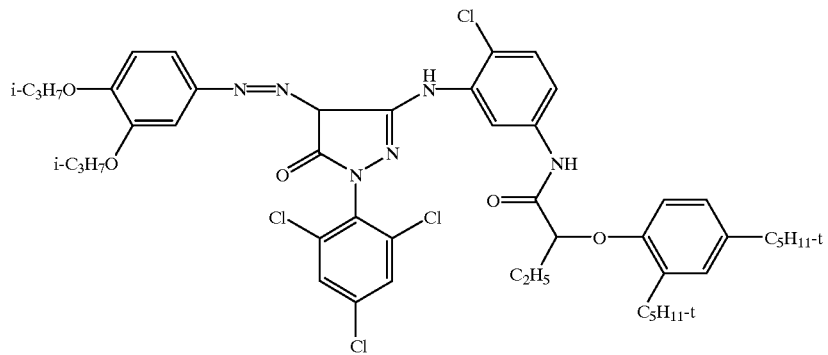
V-6
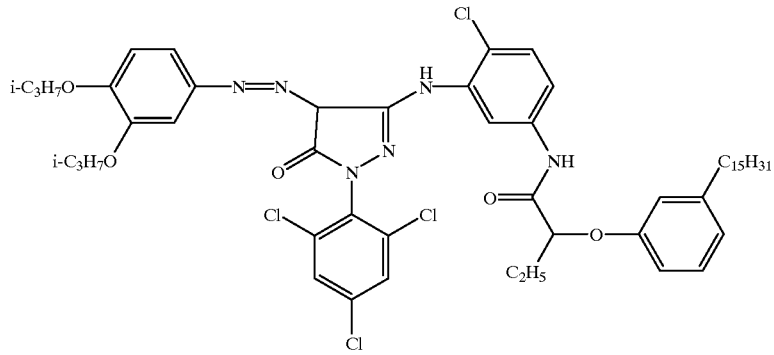

V-7
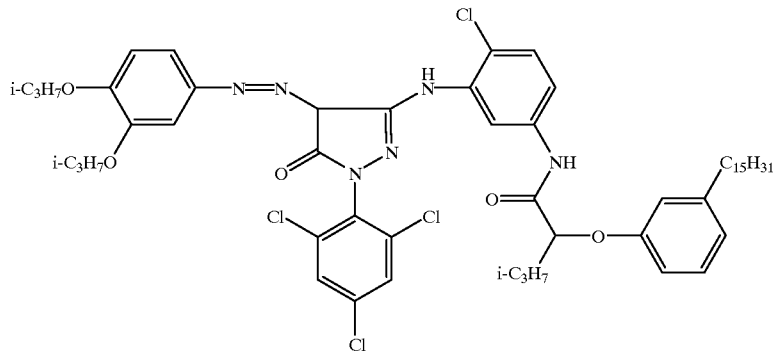
V-8
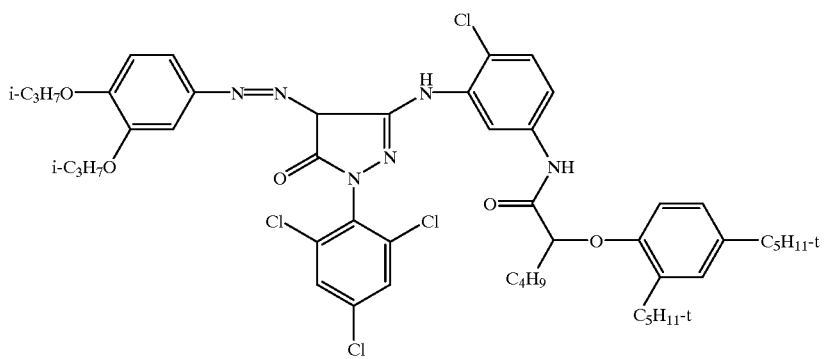
V-9 V-10
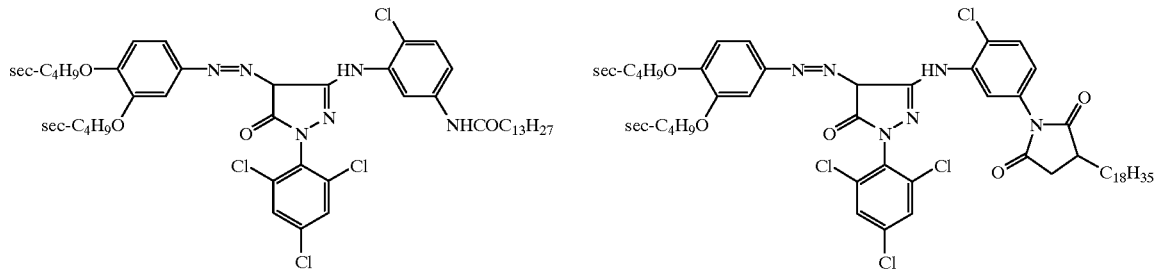
V-11 V-12
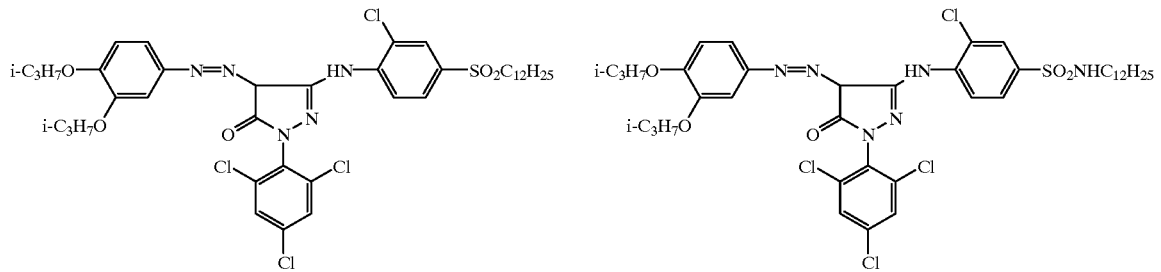

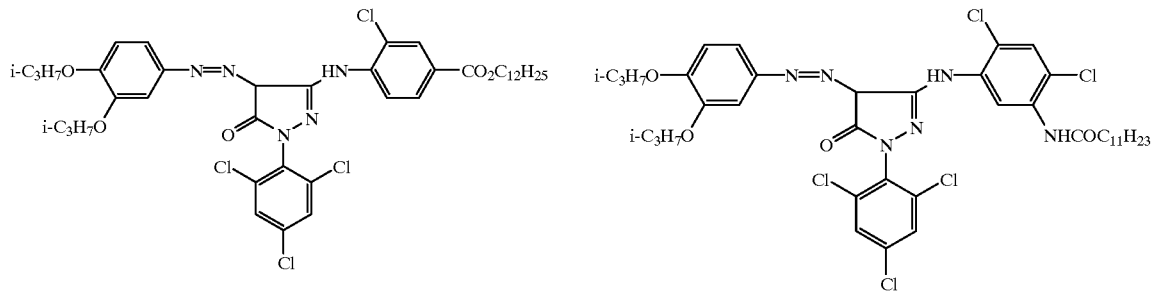
V-13
V-14
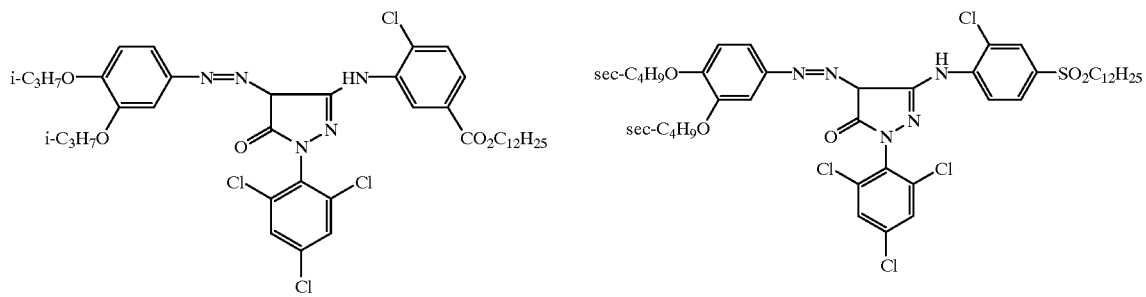
V-15
V-16
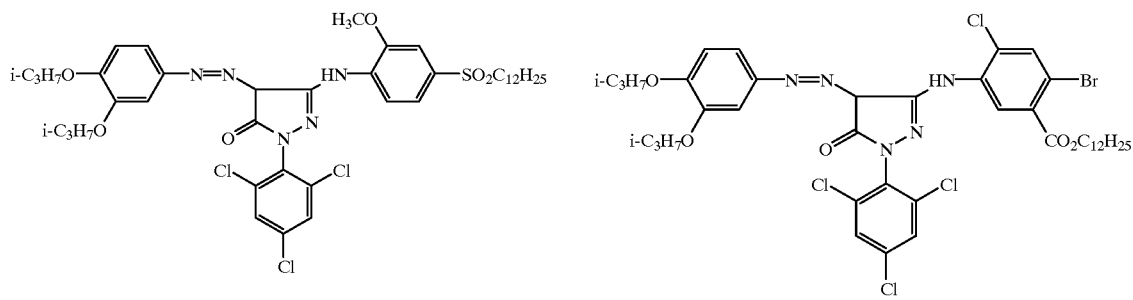
V-17
V-18
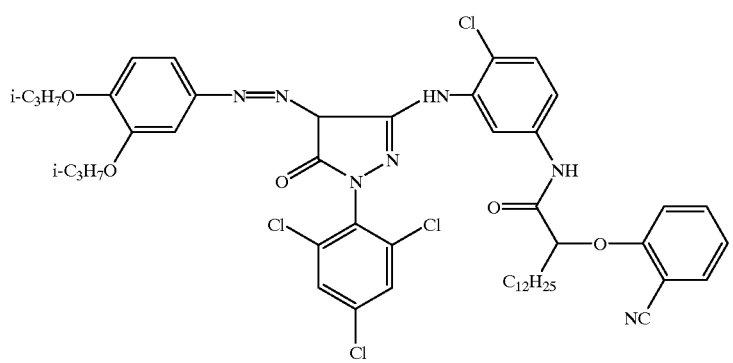
V-19

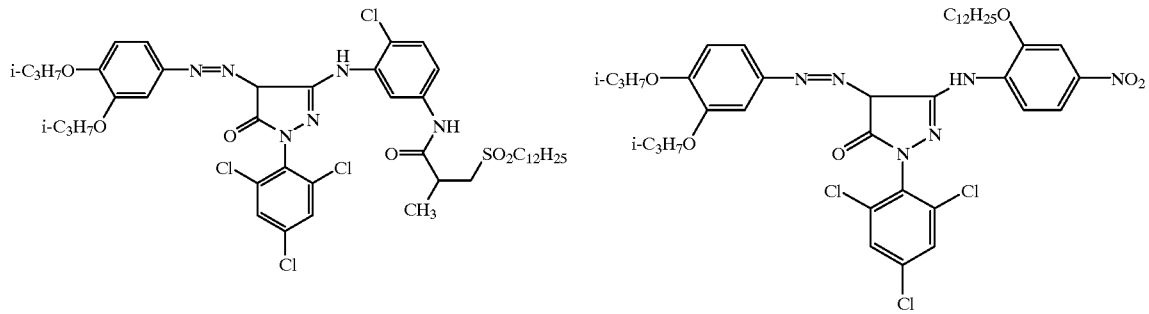

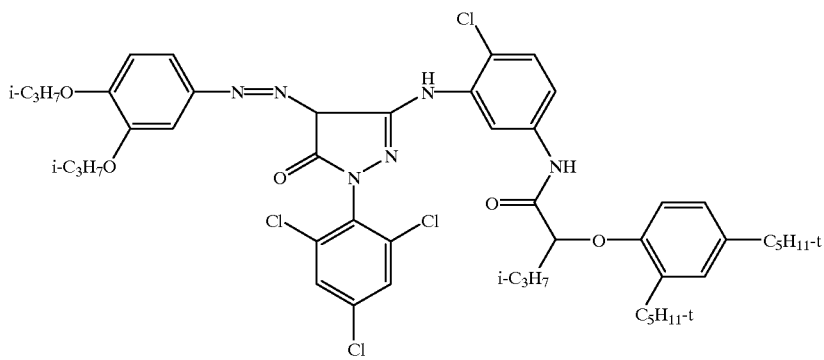

Next, exemplary synthesis of the compound represented by formulas (I) or (II) is described below.

SYNTHESIS EXAMPLE 1

(Synthesis of exemplified Compound II-1)

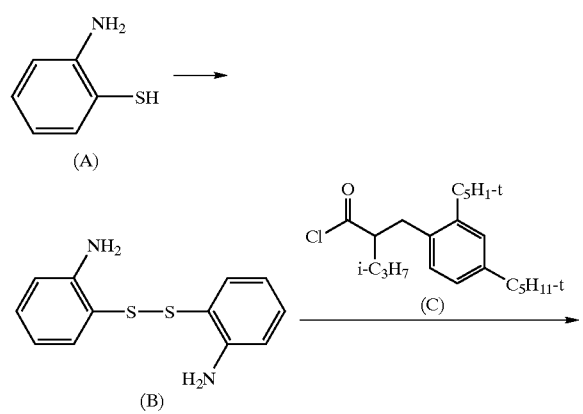

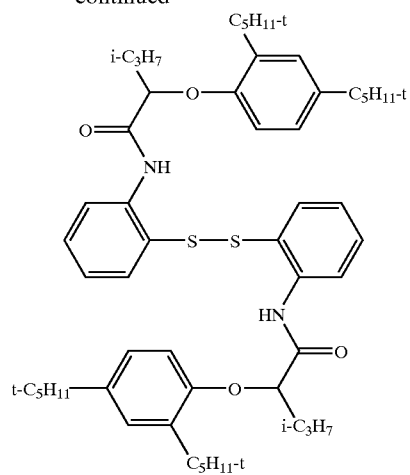

Exemplified Compound II-1

In 620 ml of ethyl acetate, 122.8 g of raw material (A) was dissolved and then cooled with ice. Subsequently, 53.8 g of 31% hydrogen peroxide was dropwise added thereto at an internal temperature of 15° C. or lower (in about 20 min.). After completing the addition, stirring continued further for 1 hr. at a temperature at 20° C. or lower. Then, to the reaction mixture was added 194 g of potassium carbonate dissolved in 340 ml water. Subsequently, 450 g of compound (C) dissolved in 450 ml of ethyl acetate was dropwise added at an internal temperature of 20 to 25° C. (in about 50 min.). After completing the addition, stirring continued further for 8 hrs. at room temperature. As crystals were precipitated, the reaction mixture was heated to an internal temperature of 65° C. with stirring and after dissolving the crystals, a water phase was removed. The remaining organic phase was washed with 390 ml of an aqueous 5% sodium sulfite solution and then twice with 390 ml of hot water. Since precipitation easily occurred, the above washing was carried out, while being maintained at 65° C. After distilling out ethyl acetate under reduced pressure, obtained crude crystals were washed 1,160 ml of methanol, while boiling and suspending. After cooling to room temperature, crystals were filtered and washed with 190 ml of methanol, three times. After drying at 50° C., 386.2 g of exemplified compound II-1 was obtained. The structure was identified by NMR and mass spectrum.

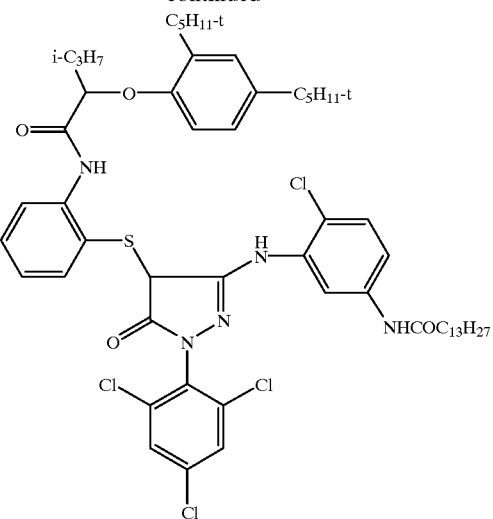

Exemplified Compound I-1

SYNTHESIS EXAMPLE 2

(Synthesis of exemplified Compound I-1)

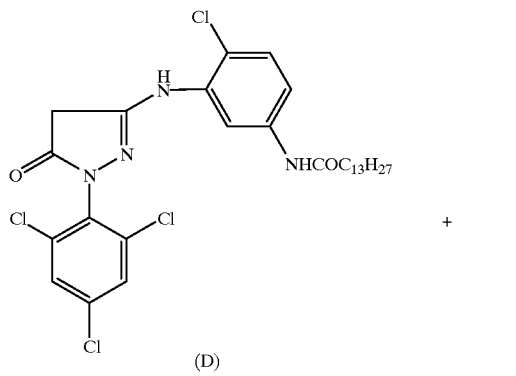

(D)

+

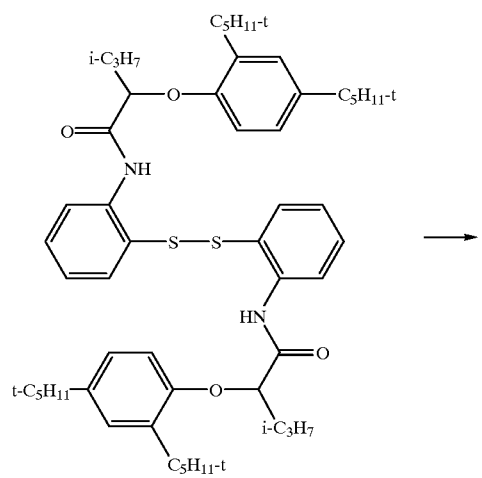

Exemplified Compound II-1

→

To 1.3 lit. of ethyl acetate, 130 g of exemplified compound II-1 and 165 g of raw material (D) was added and after dissolved at 50° C., the mixture was allowed to stand until cooled to room temperature. Subsequently, 55.7 g of potassium carbonate dissolved in 220 ml water was added thereto and 400 ml of dimethylformamide was added. After stirring for 1 hr. at room temperature, 20 ml of hypochlorous acid (measure effective chlorine concentration of 3.49%) was dropwise added five times at 30 min. intervals. As raw material (D) still remained, 30 ml of hypochlorous acid was further added thereto. After stirring for one night, an organic phase was washed with 500 ml of hot water. Then, the organic phase was washed successively with the following aqueous solutions having composition described below.

| Washing 1: | 27 g | sodium sulfite/550 ml water |
| Washing 2: | 550 ml | saturated sodium chloride solution |
| Washing 3: | 32 ml | concentrated hydrochloric acid/ |
|  | 550 ml | saturated sodium chloride solution |
| Washing 4: | 550 ml | saturated sodium chloride solution, 3 times. |

After completion of washing, ethyl acetate was distilled out under reduced pressure. Adding 290 ml of ethyl acetate, the obtained crude crystals were dissolved and then recrystalized adding 570 ml of acetonitrile. Further, through recrystalization in a mixed solvent of 820 ml ethyl acetate and 260 ml acetonitrile was obtained 123.6 g of exemplified compound II-1. No contamination of exemplified compound II-1 was observed (less than 0.1%). The structure was identified by NMR and mass spectrum.

The magenta coupler represented by formula (I) is used preferably in an amount of $1\times10^{-3}$ to $8\times10^{-1}$, and more preferably $\times10^{-2}$ to $3\times10^{-1}$ mol/mol AgX. The magenta coupler of formula (I) may be used in combination with other kind of a magenta coupler. The compound represented by formula (II) is used preferably in an amount of 0.1 to 10% by weight, and more preferably 0.5 to 5% by weight, based on the magenta coupler of formula (I). The DIR coupler represented by formula (III) (I) is used preferably in an amount of $1\times10^{-5}$ to $5\times10^{-1}$, and more preferably $1\times10^{-3}$ to $1\times10^{-1}$ mol/mol AgX. The DIR coupler of formula (III) may be used in combination with other kind of a DIR coupler. The DIR coupler represented by formula (IV) (I) is used preferably in an amount of $1 \times 10^{-5}$ to $5 \times 10^{-1}$, and more preferably $1 \times 10^{-3}$ to $2 \times 10^{-1}$ mol/mol AgX. The DIR coupler of formula (IV) may be used in combination with other kind of a DIR coupler. The colored coupler represented by formula (V) is used preferably in an amount of 5 to 50% by weight, and more preferably 10 to 30% by weight, based on the magenta coupler of formula (I).

The method for incorporating the compounds of formulas (I) through (V) is not specifically limited and any of methods known in conventional photographic materials are employable, including dispersion as fine oil particles through dissolution in a high boiling solvent, as described in U.S. Pat. No. 2,320,027; dispersion through dissolution by introducing a ballast group and a water-solubilizing group, as described in U.S. Pat. No. 2,186,849; integrating into a polymeric compound as its component, as described in U.S. Pat. No. 2,397,864; a method of filling in a latex polymer and dispersing through mechanical crushing by the use of a colloid mill or the like.

The color photographic material according to this invention comprises on a support a green-sensitive silver halide emulsion layer containing the compounds of formulas (I) through (V), as a basic constitution, and a multicolor photographic material is desirable. Thus, according to one of preferred embodiments of this invention, the color photographic material comprises a support provided thereon a green-sensitive silver halide emulsion layer containing the compounds of formulas (I) through (V), which is in combination a blue-sensitive silver halide emulsion layer containing a yellow coupler (such as benzoylacetoanilide compounds and pivaloylacetoanilide compounds) and a red-sensitive silver halide emulsion layer containing a cyan coupler (such as naphthol compounds, 2-ureido-5-acylaminophenol compounds). In addition thereto, a filter layer, a protective layer, an interlayer, a sublayer or a backing layer may be optionally provided. Further, the silver halide emulsion layer having sensitivity within each of the wavelength region may be comprised of two or more layers.

Silver halide emulsions used in this invention include not only silver chloride, silver bromide and silver iodide, but also mixed silver halide such as silver chlorobromide, silver iodobromide, silver iodochloride or silver iodochlorobromide. These silver halide emulsions can be prepared according to the conventional methods, and ammoniacal precipitation, neutral precipitation, acidic precipitation, a halide conversion method, variable addition and uniform precipitation are applicable. The mean grain size is not specifically limited but is preferably 0.01 to 5 $\mu$m. Two or more silver halide emulsions which have been separately prepared may be blended. The silver halide emulsions used in this invention can be chemically sensitized by the commonly known methods, including a gold sensitization with a gold complex, reduction sensitization with a reducing compound, sulfur sensitization using a compound containing a reactive sulfur with a silver ion or active gelatin, and sensitization with noble metal salts of the VIII group of the periodical table. The silver halide emulsions can be spectrally sensitized using cyanine dyes such as monomethine cyanines, pentamethine cyanines, merocyanines and carbocyanines, alone or in combination thereof, or in combination with styryl dyes or aminostilbene compounds.

Furthermore, a commonly known stablilizer, antifoggant, surfactant, defoaming agent, antistatic agent, hardener, agent for improving physical properties of the layer, brightening agent, anti-staining agent, UV absorbent, and anti-irradiation agent. Compounds described in Research Disclosure (also denoted as RD vol. 176, No. 17643 (1978)can be employed as the foregoing additives.

Supports used in the color photographic material of this invention are optionally selected according to its purpose. Examples of the supports include cellulose acetate film, polyethylene terephthalate (PET) film, polystyrene (PS) film, polycarbonate (PC) film, or their lamination materials; paper, baryta paper, α-olefin polymer-laminated paper, synthetic paper, glass and metals.

In the photographic material of this invention, gelatin is advantageously employed as binder or protective colloid; and other hydrophilic colloids including gelatin derivatives, graft polymers of gelatin with other polymers, cellulose derivatives such as hydroxyethyl cellulose, carboxymethyl cellulose and cellulose sulfuric acid ester, and hydrophilic synthetic polymer compounds such as polyvinyl alcohol, partial acetals of polyvinyl alcohol, poly-N-vinylpyrrolidone, polyacrylic acid, polymethacrylic acid, polyacrylamide and their copolymers may be used in combination with gelatin.

The color photographic materials, after exposure, are subjected to conventional color development. The basic process of the negative-positive method comprises color development, bleach and fixing. The basic process of the reversal method comprises the first development, followed by exposure to white light or treatment in a foggant-containing bath, and the steps of color development, bleach and fixing. Each of these steps may be independently carried out. Alternatively, two or more steps may be conducted at one time using a processing solution having such functions. Example thereof include color processing with a monobath containing a color developing agent, a ferric salt bleaching component and a thiosulfate fixing component (as described in JP-B No. 35-1885); and a monobath bleach-fixing method containing a bleaching component of a ethylenediaminetetraacetate iron (III) complex and a thiosulfate fixing component.

Photographic processing usable in this invention is not specifically limited and any of photographic processing methods is applicable. Representative examples thereof are as follows:

(1) color development, followed by bleach-fixing, and optionally, washing and stabilization treatment;

(2) color development, followed by bleaching and fixing, and further optionally washing and stabilization treatment;

(3) pre-hardening, followed by neutralization, color development, stop-fixing, washing, bleaching, washing, post-hardening and washing;

(4) color development, followed by washing, auxiliary color development, stopping, bleaching, fixing, washing and stabilization; and (5) a method of processing a low silver coverage, silver halide photographic material using an amplifier such as peroxides or cobalt complex salts.

The processing may be conducted at a high temperature of 30° C. or more, at room temperature or at a low temperature of 20° C. or less, but in general, carried out at a temperature of 20 to 70° C. The temperature of these steps may be the same or different.

EXAMPLES

Embodiment s of this invention will be described based on examples but are limited by no means to these examples.

Example 1

Preparation of Color Photographic Material

On a triacetyl cellulose film support were formed the following layers containing composition as shown below to prepare a multi-layered color photographic material Sample 101. The addition amount of each compound was represented in term of g/m², provided that the amount of silver halide or colloidal silver was converted to the silver amount and the amount of a sensitizing dye was represented in mol/Ag mol.

| 1st Layer (Anti-Halation Layer) | |
|---|---|
| Black colloidal silver | 0.16 |
| UV absorbent (UV-1) | 0.30 |
| Colored magenta coupler (CM-1) | 0.12 |
| Colored cyan coupler (CC-1) | 0.03 |
| High boiling solvent (OIL-1) | 0.24 |
| Gelatin | 1.33 |
| 2nd Layer (Intermediate Layer) | |
| Silver iodobromide emulsion j | 0.10 |
| Anti-staining agent (AS-1) | 0.12 |
| High boiling solvent (OIL-1) | 0.15 |
| Gelatin | 0.67 |
| 3rd Layer (Low-speed Red-Sensitive Layer) | |
| Silver iodobromide emulsion c | 0.053 |
| Silver iodobromide emulsion d | 0.11 |
| Silver iodobromide emulsion e | 0.11 |
| Sensitizing dye (SD-1) | $2.2 \times 10^{-5}$ |
| Sensitizing dye (SD-2) | $5.9 \times 10^{-5}$ |
| Sensiziting dye (SD-3) | $1.2 \times 10^{-4}$ |
| Sensitizing dye (SD-4) | $1.6 \times 10^{-4}$ |
| Sensitizing dye (SD-5) | $1.6 \times 10^{-4}$ |
| Cyan coupler (C-1) | 0.19 |
| Colored cyan coupler (CC-1) | 0.003 |
| High boiling solvent (OIL-2) | 0.096 |
| Anti-staining agent (AS-2) | 0.001 |
| Gelatin | 0.44 |
| 4th Layer (Medium-speed Red-sensitive Layer) | |
| Silver iodobromide emulsion b | 0.28 |
| Silver iodobromide emulsion c | 0.34 |
| Silver iodobromide emulsion d | 0.50 |
| Sensitizing dye (SD-1) | $1.8 \times 10^{-5}$ |
| Sensitizing dye (SD-4) | $2.6 \times 10^{-4}$ |
| Sensitizing dye (SD-5) | $2.8 \times 10^{-4}$ |
| Cyan coupler (C-1) | 0.74 |
| Colored cyan coupler (CC-1) | 0.081 |
| DIR compound (DI-1) | 0.020 |
| DIR compound (DI-4) | 0.008 |
| High boiling solvent (OIL-2) | 0.42 |
| Anti-staining agent (AS-2) | 0.003 |
| Gelatin | 1.95 |
| 5th Layer (High-speed Red-Sensitive Layer) | |
| Silver iodobromide emulsion a | 1.45 |
| Silver iodobromide emulsion e | 0.076 |
| Sensitizing dye (SD-1) | $2.3 \times 10^{-5}$ |
| Sensitizing dye (SD-2) | $1.1 \times 10^{-4}$ |
| Sensitizing dye (SD-3) | $1.5 \times 10^{-5}$ |
| Sensitizing dye (SD-4) | $2.1 \times 10^{-4}$ |
| Cyan coupler (C-2) | 0.087 |
| Cyan coupler (C-3) | 0.12 |
| Colored cyan coupler (CC-1) | 0.036 |
| DIR compound (DI-1) | 0.021 |
| DIR compound (DI-3) | 0.005 |
| Bleach-accelerating agent releasing coupler (BAR-1) | 0.022 |
| High boiling solvent (OIL-2) | 0.15 |
| Anti-staining agent (AS-2) | 0.004 |
| Gelatin | 1.40 |
| 6th Layer (Intermediate Layer) | |
| Dye (F-1) | 0.03 |
| Anti-staining agent (AS-1) | 0.18 |
| High boiling solvent (OIL-1) | 0.22 |
| Gelatin | 1.00 |
| 7th Layer (Low-speed Green-Sensitive Layer) | |
| Silver iodobromide emulsion c | 0.22 |
| Silver iodobromide emulsion e | 0.22 |
| Sensitizing dye (SD-6) | $4.7 \times 10^{-5}$ |
| Sensitizing dye (SD-7) | $2.6 \times 10^{-4}$ |
| Sensitizing dye (SD-8) | $1.9 \times 10^{-4}$ |
| Sensitizing dye (SD-9) | $1.1 \times 10^{-4}$ |
| Sensitizing dye (SD-10) | $2.4 \times 10^{-5}$ |
| Magenta coupler (M-1) | 0.35 |
| Colored magenta coupler (CM-1) | 0.044 |
| DIR compound (DI-2) | 0.010 |
| High boiling solvent (OIL-1) | 0.41 |
| Anti-staining agent (AS-2) | 0.001 |
| Anti-staining agent (AS-3) | 0.11 |
| Gelatin | 1.29 |
| 8th Layer (Medium-speed Green-Sensitive Layer) | |
| Silver iodobromide emulsion b | 0.90 |
| Silver iodobromide emulsion e | 0.048 |
| Sensitizing dye (SD-6) | $3.8 \times 10^{-5}$ |
| Sensitizing dye (SD-7) | $2.6 \times 10^{-5}$ |
| Sensitizing dye (SD-8) | $3.4 \times 10^{-4}$ |
| Sensitizing dye (SD-9) | $1.6 \times 10^{-4}$ |
| Sensitizing dye (SD-10) | $4.4 \times 10^{-5}$ |
| Magenta coupler (M-1) | 0.15 |
| Colored cyan couple (CM-1) | 0.062 |
| Colored magenta coupler (CM-2) | 0.030 |
| DIR compound (DI-2) | 0.032 |
| High boiling solvent (OIL-1) | 0.28 |
| Anti-staining agent (AS-2) | 0.005 |
| Anti-staining agent (AS-3) | 0.045 |
| Gelatin | (1.00) |
| 9th Layer (High-speed Green-Sensitive Layer) | |
| Silver iodobromide emulsion a | 1.39 |
| Silver iodobromide emulsion e | 0.073 |
| Sensitizing dye (SD-6) | $4.1 \times 10^{-5}$ |
| Sensitizing dye (SD-7) | $2.6 \times 10^{-5}$ |
| Sensitizing dye (SD-8) | $3.7 \times 10^{-4}$ |
| Sensitizing dye (SD-10) | $4.9 \times 10^{-5}$ |
| Magenta coupler (M-1) | 0.071 |
| Magenta coupler (M-2) | 0.073 |
| Colored magenta coupler (CM-2) | 0.013 |
| DIR compound (DI-2) | 0.004 |
| DIR compound (DI-3) | 0.003 |
| High boiling solvent (OIL-1) | 0.27 |
| Anti-staining agent (AS-2) | 0.008 |
| Anti-staining agent (AS-3) | 0.043 |
| Gelatin | 1.35 |
| 10th Layer (Yellow Filter Layer) | |
| Yellow colloidal silver | 0.053 |
| Anti-staining agent (AS-1) | 0.15 |
| High boiling solvent (OIL-1) | 0.18 |
| Formalin scavenger (X-1) | 0.06 |
| Gelatin | 0.83 |
| 11th Layer: Low-speed Blue-sensitive Layer | |
| Silver iodobromide emulsion g | 0.22 |
| Silver iodobromide emulsion h | 0.099 |
| Silver iodobromide emulsion i | 0.17 |
| Sensitizing dye (SD-11) | $2.4 \times 10^{-4}$ |
| Sensitizing dye (SD-12) | $5.7 \times 10^{-4}$ |
| Sensitizing dye (SD-13) | $1.3 \times 10^{-4}$ |
| Yellow coupler (Y-1) | 1.02 |
| Bleach-accelerating agent releasing coupler (BAR-1) | 0.022 |
| High boiling solvent (OIL-1) | 0.42 |
| Anti-staining agent (AS-2) | 0.003 |
| Formaline scavenger (X-1) | 0.11 |
| Formaline scavenger (X-2) | 0.18 |
| Gelatin | 1.95 |
| 12th Layer (High-sped Blue-sensitive Layer) | |
| Silver iodobromide emulsion f | 1.52 |

| | |
|---|---|
| Sensitizing dye (SD-11) | $8.3 \times 10^{-5}$ |
| Sensitizing dye (SD-12) | $2.3 \times 10^{-4}$ |
| Yellow coupler (Y-1) | 0.22 |
| DIR compound (DI-5) | 0.11 |
| High boiling solvent (OIL-1) | 0.13 |
| Anti-staining agent (AS-2) | 0.003 |
| Formaline scavenger (X-1) | 0.15 |
| Formaline scavenger (X-2) | 0.20 |
| Gelatin | 1.20 |
| 13th Layer: First Protective Layer | |
| Silver iodobromide emulsion k | 0.30 |
| UV absorbent (UV-1) | 0.11 |
| UV absorbent (UV-2) | 0.055 |
| Liquid paraffin | 0.28 |
| Formaline scavenger (X-1) | 0.079 |
| Gelatin | 1.00 |
| 14th Layer (Second protective Layer) | |
| Matting agent PM-1 | 0.13 |
| Matting agent PM-2 | 0.018 |
| Lubricant (WAX-1) | 0.021 |
| Gelatin | 0.55 |

Characteristics of silver iodobromide emulsions described above are shown below, in which the average grain size refers to an edge length of a cube having the same volume as that of the grain.

| Emulsion | Av. grain size ($\mu$m) | Av. AgI content (mol %) | Diameter/thickness ratio |
|---|---|---|---|
| a | 0.85 | 4.2 | 7.0 |
| b | 0.70 | 4.2 | 6.0 |
| c | 0.50 | 4.2 | 5.0 |
| d | 0.38 | 8.0 | Octahedral |
| e | 0.27 | 2.0 | Tetradecahedral |
| f | 1.00 | 8.0 | 4.5 |
| g | 0.74 | 3.5 | 6.2 |
| h | 0.44 | 4.2 | 6.1 |
| i | 0.30 | 1.9 | 5.5 |
| j | 0.03 | 2.0 | 1.0 |

The thus prepared emulsions d and f were added with sensitizing dyes afore-described and ripened, and then chemically sensitized by adding triphenylphosphine selenide, sodium thiosulfate, chloroauric acid and potassium thiocyanate until relationship between sensitivity and fog reached an optimum point. Silver iodobromide emulsions a, b, c, g, h, and i were each spectrally and chemically sensitized in a manner similar to silver iodobromide emulsions d and f.

In addition to the above composition were added coating aids SU-1, SU-2 and SU-3; a dispersing aid SU-4; viscosity-adjusting agent V-1; stabilizers ST-1 and ST-2; fog restrainer AF-1 and AF-2 comprising two kinds polyvinyl pyrrolidone of weight-averaged molecular weights of 10,000 and 1.100,000; inhibitors AF-3, AF-4 and AF-5; hardener H-1 and H-2; and antiseptic Ase-1.

Chemical formulas of compounds used in the Samples described above are shown below.

SU-1: $C_8F_{17}SO_2N(C_3H_7)CH_2COOK$
SU-2: $C_8F_{17}SO_2NH(CH_2)_3N^+(CH_3)_3Br^-$
SU-3: Sodium di-(2-ethylhexyl) sulfosuccinate
SU-4: Tri-i-propylnaphthalenesulfonic acid sodium salt
ST-1: 4-hydroxy-6-methyl-1,3,3a,7-tetraazaindene
ST-2: Adenine
AF-3: 1-Phenyl-5-mercaptotetrazole
AF-4: 1-(4-Carboxyphenyl)-5-mercaptotetrazole
AF-5: 1-(3-Acetoamidophenyl)-5-mercaptotetrazole
H-1: $[CH_2\!=\!CHSO_2CH_2)_3CCH_2SO_2CH_2CH_2]_2 NCH_2CH_2SO_3K$
H-2: 2,4-Dichloro-6-hydroxy-s-triazine sodium salt
AS-1: 2,5-Bis(1,1-dimethyl-4-hexyloxycarbonylbutyl)-hydroquinone
As-2: Dodecyl gallate
AS-3: 1,4-Bis(2-tetradecyloxycarbonylethyl)piperazine
OIL-1: Tricresyl phosphate
OIL-2: Di(2-ethylhexyl)phthalate
X-1: Allantoin (5-ureidohydantoin)
X-2: Hydantoin

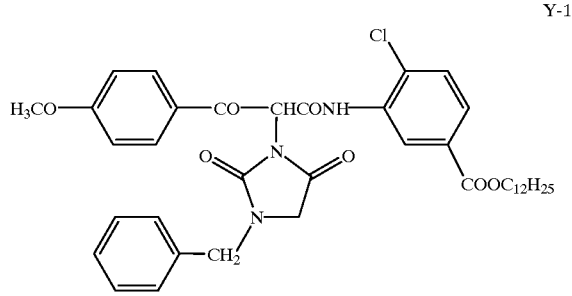

Y-1

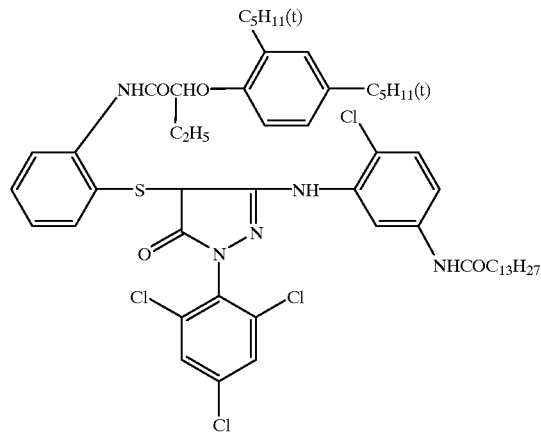

M-1

-continued
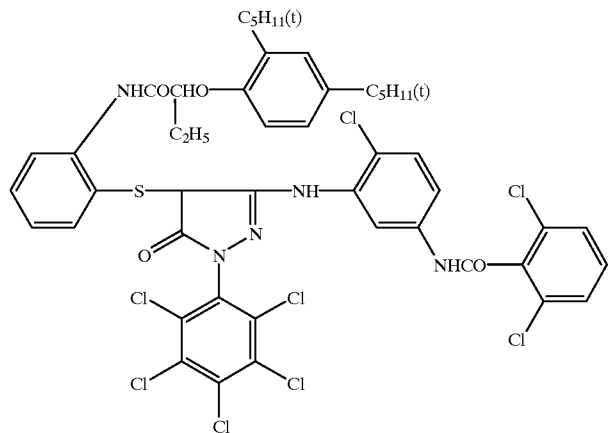
M-2
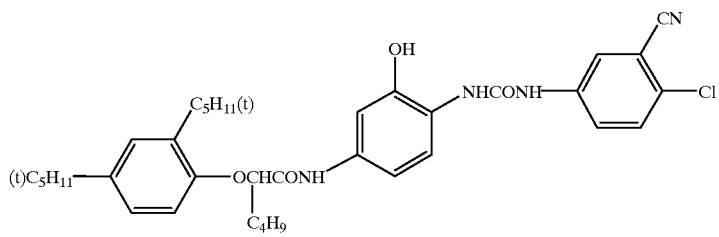
C-1
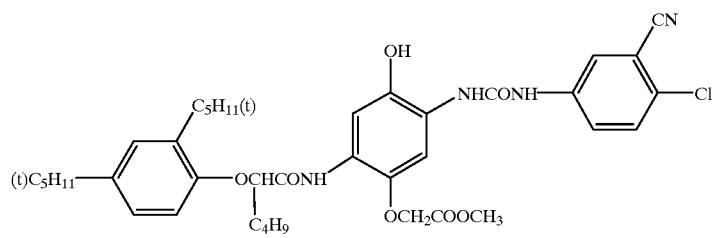
C-2
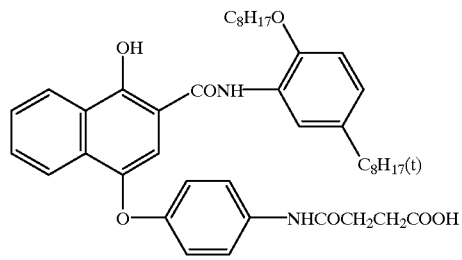
C-3
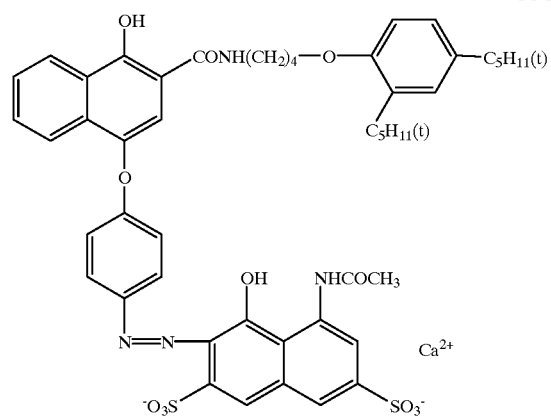
CC-1

-continued
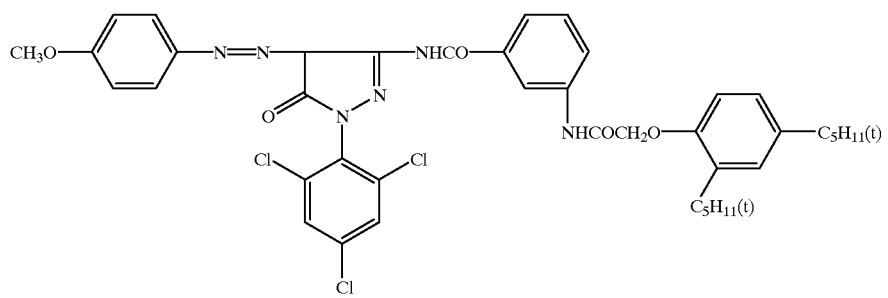
CM-1
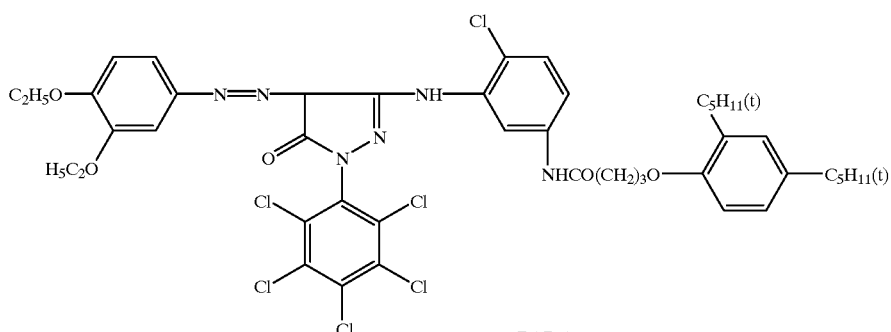
CM-2
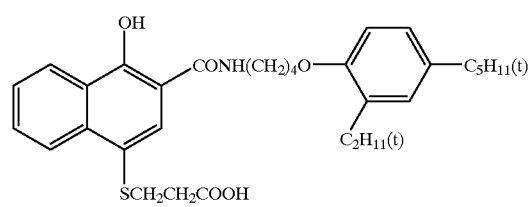
BAR-1
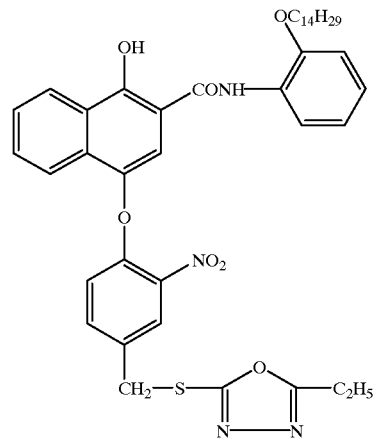
DI-1
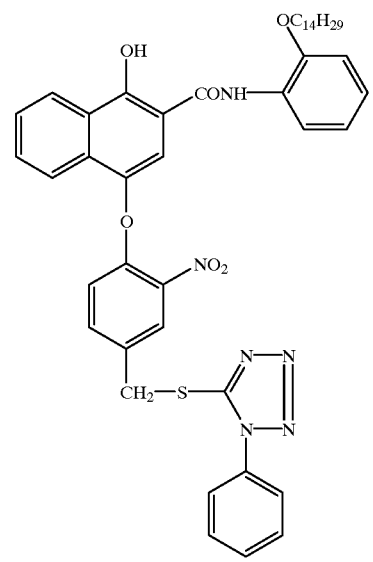
DI-2
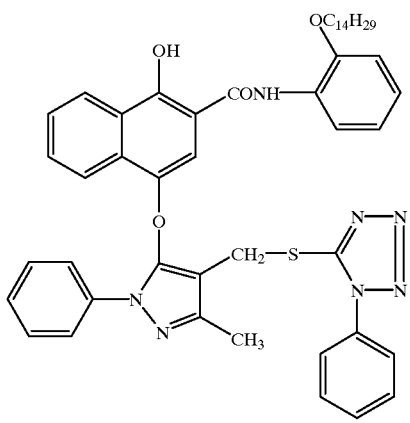
DI-3

-continued
DI-4
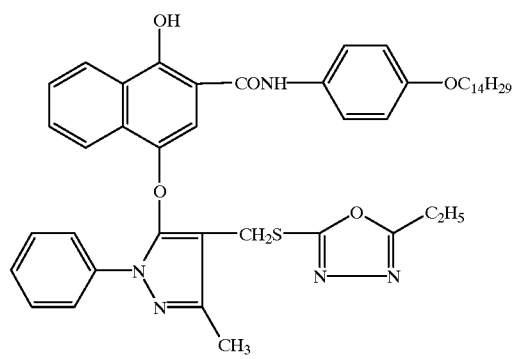
DI-5
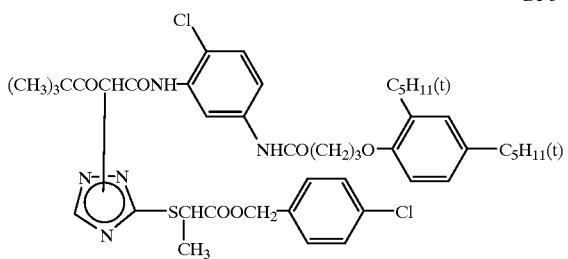
UV-1
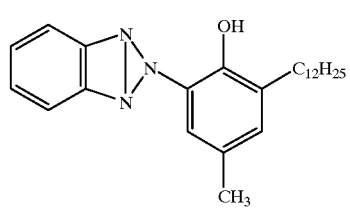
UV-2
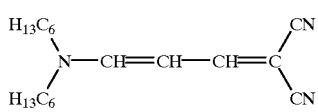
V-1
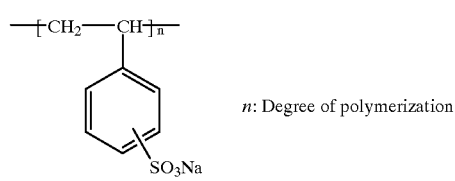
$n$: Degree of polymerization
Ase-1 (mixture)
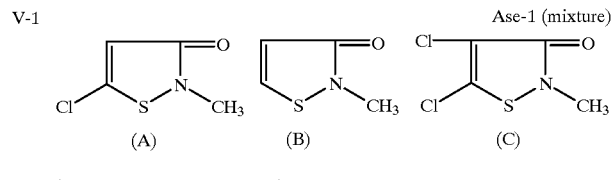
(A:B:C = 50:46:4, molar ratio)
SD-1
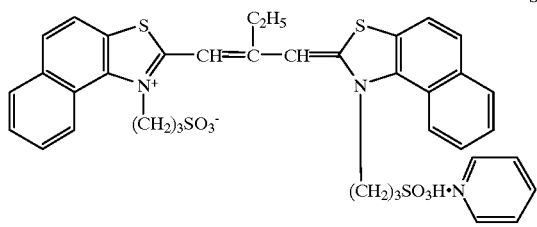
SD-2
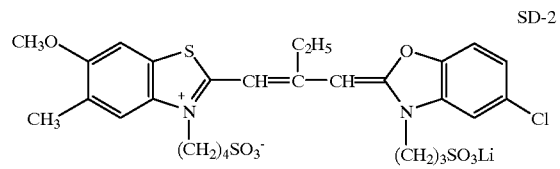
SD-3
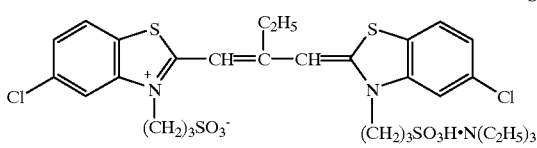
SD-4
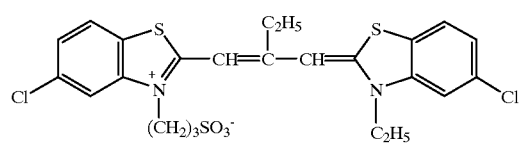
SD-5
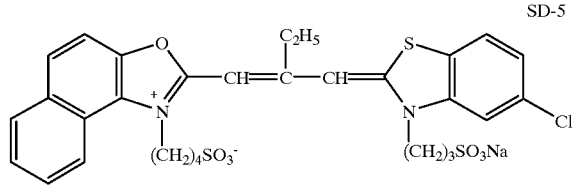
SD-6
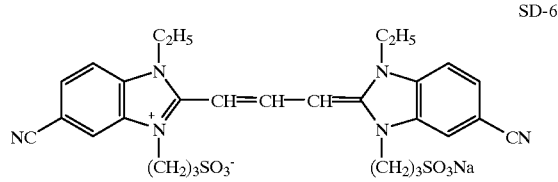
SD-7
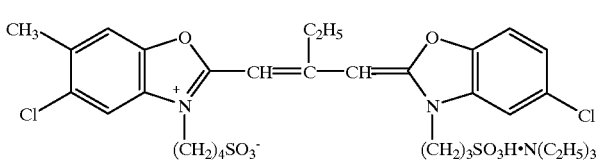

SD-8
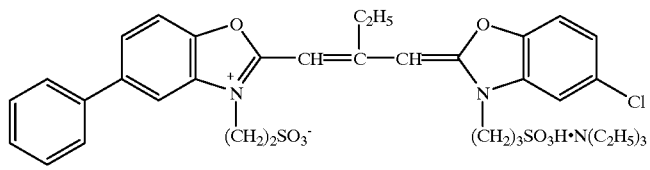

SD-9
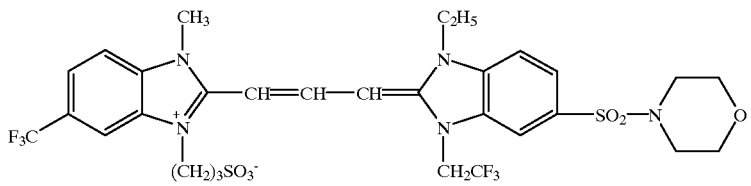

SD-10
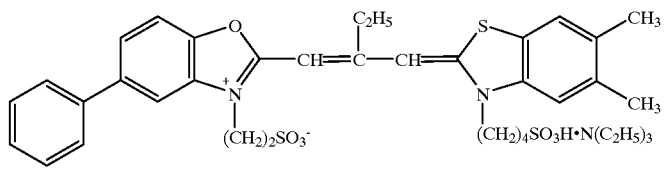

SD-11
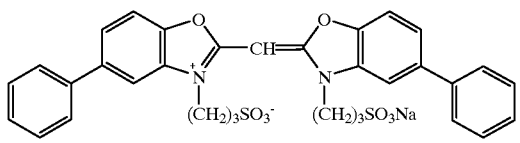

SD-12
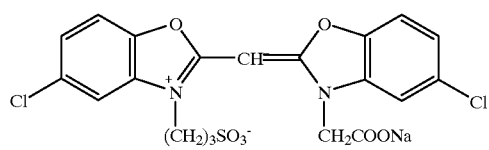

SD-13
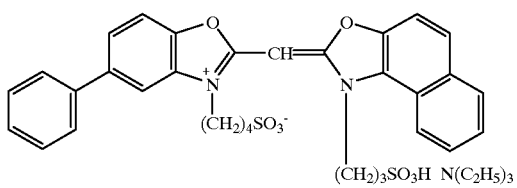

F-1
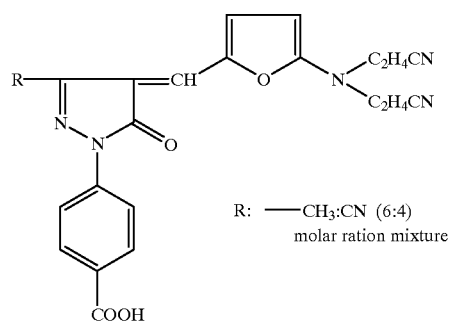

R: —CH$_3$:CN (6:4) molar ration mixture

WAX-1
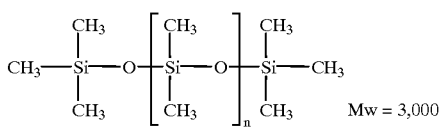
Mw = 3,000

PM-1
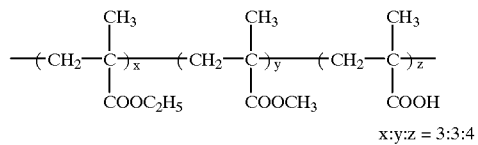
x:y:z = 3:3:4

PM-2
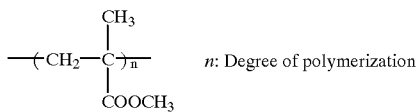
n: Degree of polymerization

Samples 102 through 123 were prepared in the same manner as Sample 101, except in the 7th layer (intermediate speed green-sensitive layer), magenta coupler (M-1) was replaced by an equimolar amount of a comparative coupler or an inventive coupler, DIR coupler (DI-2) was replaced by an equimolar amount of a comparative DIR coupler or the DIR coupler of formula (III) or (IV), colored coupler (CM-2) was replaced by an equimolar amount of a comparative colored coupler or the colored coupler of formula (V), or the magenta coupler of formula (II) of 2% by weight was added.

TABLE 1

| Sample No. | Magenta Coupler | Compd. of Formula (II) | DIR Coupler | Colored Coupler |
|---|---|---|---|---|
| 101 (comp.) | M-1 | — | DI-2 | CM-2 |
| 102 (comp.) | M-A | — | DI-2 | CM-2 |
| 103 (comp.) | M-B | — | DI-2 | CM-2 |
| 104 (comp.) | M-1 | — | DI-A | CM-2 |

TABLE 1-continued

| Sample No. | Magenta Coupler | Compd. of Formula (II) | DIR Coupler | Colored Coupler |
|---|---|---|---|---|
| 105 (comp.) | M-1 | — | DI-B | CM-2 |
| 106 (comp.) | M-1 | — | DI-2 | CM-A |
| 107 (inv.) | I-1 | — | DI-2 | CM-2 |
| 108 (inv.) | I-2 | — | DI-2 | CM-2 |
| 109 (inv.) | I-25 | — | DI-2 | CM-2 |
| 110 (inv.) | I-1 | II-1 | DI-2 | CM-2 |
| 111 (inv.) | I-2 | II-2 | DI-2 | CM-2 |
| 112 (inv.) | I-25 | II-1 | DI-2 | CM-2 |
| 113 (inv.) | I-1 | II-2 | III-2 | CM-2 |
| 114 (inv.) | I-2 | — | III-3 | CM-2 |
| 115 (inv.) | I-25 | II-1 | III-6 | CM-2 |
| 116 (inv.) | I-1 | II-1 | IV-1 | CM-2 |
| 117 (inv.) | I-2 | II-2 | IV-2 | CM-2 |
| 118 (inv.) | I-25 | — | IV-3 | CM-2 |
| 119 (inv.) | I-1 | II-1 | III-2 | V-1 |
| 120 (inv.) | I-2 | II-2 | IV-1 | V-1 |
| 121 (inv.) | I-25 | — | IV-1 | V-6 |
| 122 (inv.) | I-1 | II-1 | IV-1 | V-1 |
| 123 (inv.) | I-1 | — | DI-2 | V-1 |

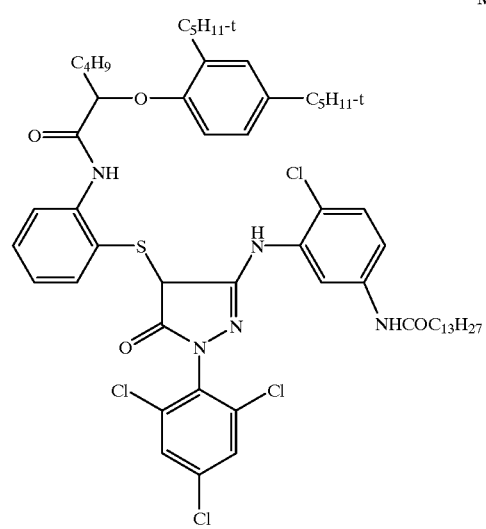

M-A

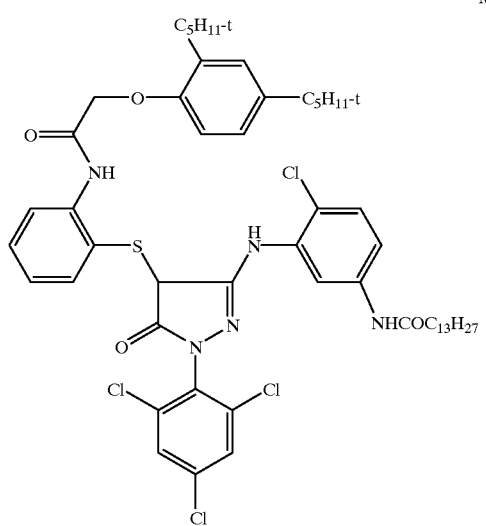

M-B

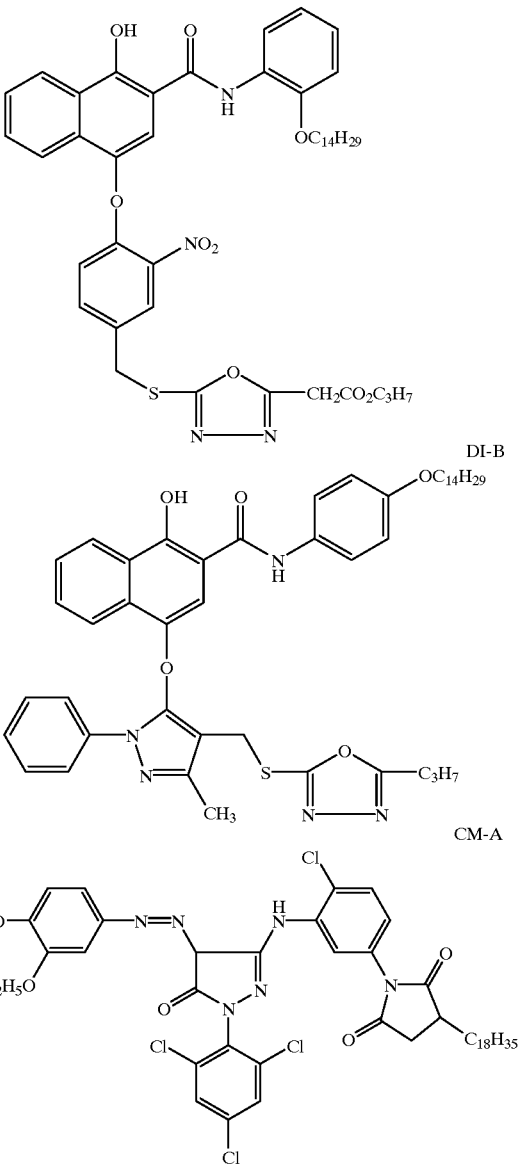

The thus prepared Samples 101 through 123 were evaluated with respect to photographic characteristics.

Sensitivity

Samples each were exposed to white light through an optical wedge and processed following to the process described below to determine sensitivity. Sensitivity is represented by a relative value of the reciprocal of exposure giving a density of a minimum density (or fog density) plus 0.7, based on the sensitivity of Sample 101 being 100.

Raw stock stability

Samples each were cut to a 135-size, put into a patrone, allowed to stand under an atmosphere of 22° C. and 55% RH for conditioning and then packed into a plastic resin case months, then processed according to the process described below and evaluated with respect to sensitivity. Results there of are shown by a relative value, based on the sensitivity of Sample 101 before storage being 100.

Image storage stability

After exposed to white light, samples each were processed according to the process described below. The thus obtained samples were kept for 3 days under an atmosphere of 50° C. and 80% RH and density variation was determined with respect to a magenta density of 1.0 before storage. In this case, "+" refers to sensitization and "−" refers to desensitization.

Evaluation results are shown in Table 2.

| Processing: Processing step | Time | Temperature | Replenishing rate* |
|---|---|---|---|
| Color developing | 3 min. 15 sec. | 38 ± 0.3° C. | 780 ml |
| Bleaching | 45 sec. | 38 ± 2.0° C. | 150 ml |
| Fixing | 1 min. 30 sec. | 38 ± 2.0° C. | 830 ml |
| Stabilizing | 1 min. | 38 ± 5.0° C. | 830 ml |
| Drying | 1 min. | 55 ± 5.0° C. | — |

*:Amounts per $m^2$ of photographic material

A color developer, bleach, fixer and stabilizer each were prepared according to the following formulas.

Color developer and replenisher thereof:

| | Worker | Replenisher |
|---|---|---|
| Water | 800 ml | 800 ml |
| Potassium carbonate | 30 g | 35 g |
| Sodium hydrogencarbonate | 2.5 g | 3.0 g |
| Potassium sulfite | 3.0 g | 5.0 g |
| Sodium bromide | 1.3 g | 0.4 g |
| Potassium iodide | 1.2 mg | — |
| Hydroxylamine sulfate | 2.5 g | 3.1 g |
| Sodium chloride | 0.6 g | — |
| 4-Amino-3-methyl-N-(β-hydroxyethyl)-aniline sulfate | 4.5 g | 6.3 g |
| Diethylenetriaminepentaacetic acid | 3.0 g | 3.0 g |
| Potassium hydroxide | 1.2 g | |

Water was added to make 1 liter in total, and the pH of the developer and its replenisher were each adjusted to 10.06 and 10.18, respectively with potassium hydroxide and sulfuric acid.

Bleach and replenisher thereof:

| | Worker | Replenisher |
|---|---|---|
| Water | 700 ml | 700 ml |
| Ammonium iron (III) 1,3-diaminopropanetetraacetic acid | 125 g | 175 g |
| Ethylenediaminetetraacetic acid | 2 g | 2 g |
| Sodium nitrate | 40 g | 50 g |
| Ammonium bromide | 150 g | 200 g |
| Glacial acetic acid | 40 g | 56 g |

Water was added to make 1 liter in total and the pH of the bleach and replenisher thereof were adjusted to 4.4 and 4.0, respectively, with ammoniacal water or glacial acetic acid.

Fixer and replenisher thereof:

| | Worker | Replenisher |
|---|---|---|
| Water | 800 ml | 800 ml |
| Ammonium thiocyanate | 120 g | 150 g |
| Ammonium thiosulfate | 150 g | 180 g |
| Sodium sulfite | 15 g | 20 g |
| Ethylenediaminetetraacetic acid | 2 g | 2 g |

Water was added to make 1 liter in total and the pH of the fixer and replenisher thereof were adjusted to 6.2 and 6.5, respectively, with ammoniacal water or glacial acetic acid.

Stabilizer and replenisher thereof:

| | |
|---|---|
| Water | 900 ml |
| p-Octylphenol/ethyleneoxide (10 mol) adduct | 2.0 g |
| Dimethylolurea | 0.5 g |
| Hexamethylenetetramine | 0.2 g |
| 1,2-benzoisothiazoline-3-one | 0.1 g |
| Siloxane (L-77, product by UCC) | 0.1 g |
| Ammoniacal water | 0.5 ml |

Water was added to make 1 liter in total and the pH thereof was adjusted to 8.5 with ammoniacal water or sulfuric acid (50%).

TABLE 2

| Sample No. | Sensitivity | Raw Stock stability*[1] | Image storage stability*[2] |
|---|---|---|---|
| 101 (comp.) | 100 | 86 | +0.06 |
| 102 (comp.) | 98 | 82 | +0.06 |
| 103 (comp.) | 94 | 80 | +0.08 |
| 104 (comp.) | 103 | 85 | +0.07 |
| 105 (comp.) | 104 | 86 | +0.06 |
| 106 (comp.) | 98 | 86 | +0.06 |
| 107 (inv.) | 102 | 96 | +0.03 |
| 108 (inv.) | 103 | 95 | +0.04 |
| 109 (inv.) | 106 | 100 | +0.04 |
| 110 (inv.) | 100 | 96 | +0.03 |
| 111 (inv.) | 102 | 98 | +0.04 |
| 112 (inv.) | 104 | 101 | +0.03 |
| 113 (inv.) | 104 | 99 | +0.02 |
| 114 (inv.) | 106 | 100 | +0.02 |
| 115 (inv.) | 108 | 104 | +0.02 |
| 116 (inv.) | 110 | 106 | +0.02 |
| 117 (inv.) | 110 | 105 | +0.02 |
| 118 (inv.) | 106 | 101 | +0.03 |
| 119 (inv.) | 104 | 102 | +0.02 |
| 120 (inv.) | 109 | 106 | +0.02 |
| 121 (inv.) | 110 | 107 | +0.02 |
| 122 (inv.) | 110 | 108 | +0.01 |
| 123 (inv.) | 102 | 99 | +0.03 |

*[1]: Sensitivity after storage
*[2]: Density variation after storage

As can be seen from Table 2, Samples Nos. 107 though 123 according to this invention exhibited little variation in sensitivity after raw stock keeping and little variation in image density after storage, as compared to Sample Nos. 101 through 106.

What is claimed is:

1. A silver halide color photographic light sensitive material comprising a support having thereon a blue-sensitive silver halide emulsion layer, a green-sensitive silver halide emulsion layer and a red-sensitive silver halide emulsion layers, wherein at least one of the silver halide emulsion layers contains a coupler represented by the following formula (I):

formula (I)

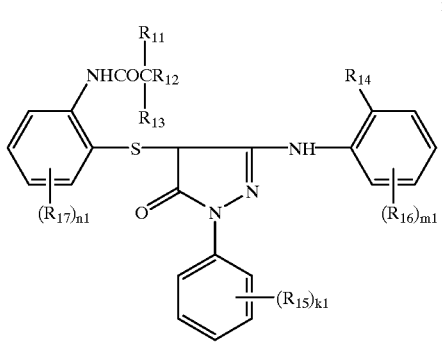

wherein $R_{11}$ represents a secondary or tertiary alkyl group, or a cycloalkyl group; $R_{12}$ represents an aryloxy group; $R_{13}$ represents a hydrogen atom, an alkyl group, a cycloalkyl group, an aryl group or a heterocyclic group; $R_{14}$ represents a halogen atom or an alkoxy group; $R_{15}$, $R_{16}$ and $R_{17}$ independently represent a substituent; k1 is an integer of 0 to 5; m1 and n1 are each an integer of 0 to 4.

2. The silver halide color photographic material of claim 1, wherein $R_{11}$ is a secondary alkyl group.

3. The silver halide color photographic material of claim 1, wherein $R_{12}$ is a substituted phenoxy group.

4. The silver halide color photographic material of claim 3, wherein $R_{12}$ is a phenoxy group substituted by at least one substituent selected from the group consisting of an alkyl group, a cycloalkyl group, an alkoxy group, a halogen atom and an alkoxycarbonyl group.

5. The silver halide color photographic material of claim 1, wherein $R_{13}$ is a hydrogen atom.

6. The silver halide color photographic material of claim 1, wherein $R_{14}$ is a chlorine atom or a methoxy group.

7. The silver halide color photographic material of claim 1, wherein $R_{15}$ is a halogen atom.

8. The silver halide color photographic material of claim 1, wherein $R_{16}$ is an acylamino group, an oxycarbonyl group, a carbamoyl group, a sulfonyl group or a sulfamoyl group.

9. The silver halide color photographic material of claim 1, wherein $R_{17}$ is a halogen atom.

10. The silver halide color photographic material of claim 1, wherein the compound of formula (I) is contained in an amount of $1 \times 10^{-3}$ to $8 \times 10^{-1}$ mol/mol Ag.

11. The silver halide color photographic material of claim 1, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (II):

formula (II)

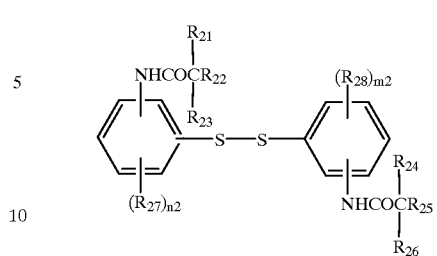

wherein $R_{21}$ and $R_{24}$ represent a secondary or tertiary alkyl group, or a cycloalkyl group; $R_{22}$ and $R_{25}$ represent an aryloxy group; $R_{23}$ and $R_{26}$ represent a hydrogen atom, an alkyl group, a cycloalkyl group, an aryl group or a heterocyclic group;

$R_{27}$ and $R_{28}$ independently represent a substituent; m2 and n2 are each an integer of 0 to 4.

12. The silver halide color photographic material of claim 11, wherein the compound of formula (II) is contained in an amount of 0.1 to 10% by weight, based on the compound of formula (1).

13. The silver halide color photographic material of claim 1, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (III):

formula (III)

wherein W represents a coupler moiety capable of forming a dye capable of being leached out of the photographic material upon reaction with an oxidation product of a color developing agent; TIME represents a timing group capable of releasing an inhibitor residue DI after being released from W upon reaction with an oxidation product of a color developing agent; and n3 is an integer of 0, 1 and 2.

14. The silver halide color photographic material of claim 13, wherein the compound of formula (III) is contained in an amount of $1 \times 10^{-3}$ to $8 \times 10^{-1}$ Ag.

15. The silver halide color photographic material of claim 1, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (IV):

formula (IV)

wherein Y represents an yellow coupler moiety capable of forming an yellow dye upon reaction with an oxidation product of a color developing agent; TIME represents a timing group capable of releasing an inhibitor residue DI after being released from Y upon reaction with an oxidation product of a color developing agent; and n4 is an integer of 0, 1 and 2.

16. The silver halide color photographic material of claim 15, wherein the compound of formula (IV) is contained in an amount of $1\times10^{-5}$ to $5\times10^{-1}$ mol/mol Ag.

17. The silver halide color photographic material of claim 1, wherein the silver halide emulsion layer containing the coupler represented by formula (I) or another silver halide emulsion layer having the same color-sensitivity as the silver halide emulsion layer containing the coupler represented by formula (I) contains a compound represented by the following formula (V):

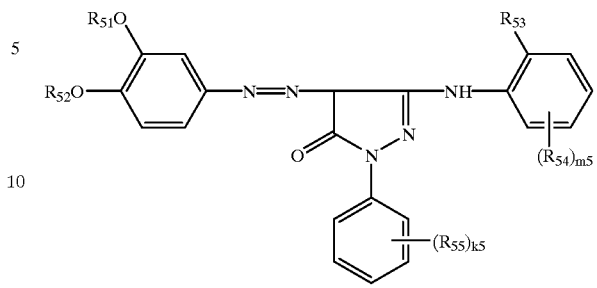

formula (V)

wherein $R_{51}$ and $R_{52}$ independently represent a secondary or tertiary alkyl group or a cycloalkyl group; $R_{53}$ represents a halogen atom or an alkoxy group; $R_{54}$ and $R_{55}$ independently represent a substituent; k5 is an integer of 0 to 5; and m5 is an integer of 0 to 4.

18. The silver halide color photographic halide material of claim 17, wherein the compound of formula (V) is contained in an amount of 5 to 50 mol %, based on the coupler of formula (I).

* * * * *